US012690752B2

(12) United States Patent
Batchelor et al.

(10) Patent No.: US 12,690,752 B2
(45) Date of Patent: Jul. 28, 2026

(54) ERGONOMIC CONTROLS FOR ENDOSCOPE

(71) Applicant: GYRUS ACMI, INC., Westborough, MA (US)

(72) Inventors: Kester Julian Batchelor, Mound, MN (US); Anthony R. Pirozzi, Raleigh, NC (US); Michael E. Callaghan, Northborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 366 days.

(21) Appl. No.: 18/306,845

(22) Filed: Apr. 25, 2023

(65) Prior Publication Data

US 2024/0115116 A1 Apr. 11, 2024

Related U.S. Application Data

(60) Provisional application No. 63/378,425, filed on Oct. 5, 2022.

(51) Int. Cl.
*A61B 1/005* (2006.01)
(52) U.S. Cl.
CPC .......... *A61B 1/0052* (2013.01); *A61B 1/0057* (2013.01)
(58) Field of Classification Search
CPC ... A61B 1/0125; A61B 1/018; A61B 1/00066; A61B 1/0052
See application file for complete search history.

(56) References Cited

U.S. PATENT DOCUMENTS

| | | | | |
|---|---|---|---|---|
| 2005/0222494 A1* | 10/2005 | Prescott | ............... | A61B 1/0615 |
| | | | | 600/113 |
| 2008/0188890 A1* | 8/2008 | Weitzner | ............ | A61B 1/00165 |
| | | | | 606/205 |
| 2010/0069712 A1* | 3/2010 | Yamaya | ............... | A61B 1/0125 |
| | | | | 600/113 |

FOREIGN PATENT DOCUMENTS

| | | |
|---|---|---|
| JP | 2011167460 | 9/2011 |
| JP | 2016532504 | 10/2016 |
| WO | 2011140118 | 11/2011 |
| WO | 2015026557 | 2/2015 |

OTHER PUBLICATIONS

"Japanese Application Serial No. 2023-92512, Notification of Reasons for Refusal mailed Sep. 17, 2024", w English translation, 11 pgs.
"Japanese Application Serial No. 2023-92512, Response filed Mar. 17, 2025 to Notification of Reasons for Refusal mailed Sep. 17, 2024", W English Claims, 12 pgs.
(Continued)

*Primary Examiner* — Alexandra L Newton
(74) *Attorney, Agent, or Firm* — Schwegman Lundberg & Woessner, P.A.

(57) ABSTRACT
A controller for an auxiliary endoscope comprises a coupling piece for attaching to a main endoscope, a handpiece connected to the coupling piece, a working shaft extending from the handpiece and extending into the coupler and a first control feature located on the handpiece for operating a pull wire extending through the working shaft, the pull wire configured to steer the auxiliary endoscope, wherein the handpiece can be moved relative to the coupling piece to adjust a position of the auxiliary scope relative to the main scope.

18 Claims, 20 Drawing Sheets

(56) References Cited

OTHER PUBLICATIONS

"Japanese Application Serial No. 2023-092512, Notification of Reasons for Rejection mailed Jun. 17, 2025", W/English Translation, 6 pgs.

"Japanese Application Serial No. 2023-092512, Response filed Sep. 17, 2025 to Notification of Reasons for Rejection mailed Jun. 17, 2025", w/ English Claims, 21 pgs.

"Japanese Application Serial No. 2023-92512, Notification of Reasons for Refusal mailed Nov. 18, 2025", W/ English Translation, 9 pgs.

"Japanese Application Serial No. 2023-092512, Response filed Feb. 17, 2026 to Notification of Reasons for Refusal mailed Nov. 18, 2025", W English Claims, 11 pgs.

"Indian Application Serial No. 202344029569, First Examination Report mailed Jan. 27, 2026", 7 pgs.

* cited by examiner

800

ERGONOMIC CONTROLS FOR ENDOSCOPE

PRIORITY CLAIM

This application claims the benefit of priority to U.S. Provisional Patent Application Ser. No. 63/378,425, filed Oct. 5, 2022, the contents of which are incorporated by reference in their entirety.

TECHNICAL FIELD

The present disclosure relates generally to medical devices comprising elongate bodies configured to be inserted into incisions or openings in anatomy of a patient to provide diagnostic or treatment operations, such as endoscopes.

More specifically, the present disclosure relates to control devices that can be attached to a proximal portion of an elongate body to control or position diagnostic or treatment devices attached to or extending from a distal portion of the elongate body.

BACKGROUND

Endoscopes can be used for one or more of 1) providing passage of other devices, e.g., therapeutic devices or tissue collection devices, toward various anatomical portions, and 2) imaging of such anatomical portions. Such anatomical portions can include the gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like.

In conventional endoscopy, the distal portion of the endoscope can be configured for supporting and orienting a therapeutic device, such as with the use of an elevator. In some systems, two endoscopes can be configured to work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path. For example, duodenoscopy procedures (e.g., Endoscopic Retrograde Cholangio-Pancreatography, hereinafter "ERCP" procedures) involve the use of an auxiliary scope (also referred to as a daughter scope or cholangioscope) that can be advanced through the working channel of a main scope (also referred to as a mother scope or duodenoscope). Furthermore, another device (e.g., a treatment device), such as a tissue retrieval device used for biopsies, can be inserted into the auxiliary scope. As such, the treatment device can be controlled and guided via pushing and pulling of the shafts of the main scope and auxiliary scope, such as via the use of pull wires extending within the shafts of the main scope and auxiliary scope. The pull wires are typically anchored at a distal end of the shaft, connected to a controller at a proximal end of the shaft, and freely slidable within the shaft therebetween. Operation of a knob or lever on the controller can cause the pull wire to induce bending of the shaft by pulling on the pull wire. Typically, pull wires are arranged in pairs to produce bending of the shaft in opposite directions.

SUMMARY

The present disclosure recognizes that problems to be solved with conventional medical devices, in particular cholangioscopes and duodenoscopes, include, among other things, 1) the difficulty of operating both a duodenoscope and a cholangioscope at the same time and 2) the difficulty of incorporating features (e.g., steerability, working channels and tissue collection features) into small-diameter devices. For example, it can be difficult to 1) easily and ergonomically operate both the cholangioscope and duodenoscope while both hands are occupied and being held in sometimes awkward positions, and 2) include two sets of two pull wires in a cholangioscope to provide four-way control due to space constraints.

The present disclosure can provide solutions to these and other problems by providing systems, devices and methods relating to ergonomic controls for endoscopes, such as cholangioscopes or other auxiliary scopes, that can be mounted to a duodenoscope and operated in a comfortable position. In examples, a first hand can be used to hold the duodenoscope and control the functions thereof, while a second hand can hold the cholangioscope and control the functions thereof. The second hand can be moved relative to the first hand to control various operations of the cholangioscope. For example, up and down movement of the second had can control retraction and advancement of the cholangioscope within the duodenoscope, while rotation of the second hand can cause rotation of the cholangioscope shaft. Rotational operability of the cholangioscope can reduce or eliminate the need for a four pull wire system, thereby freeing up space within the cholangioscope for larger working channels. The present disclosure describes a plurality of examples of controllers for an endoscope having two pull wires and rotational capabilities arranged in ergonomically advantageous ways to reduce fatigue, enhance controllability and reduce the number of pull wires compared to four pull wire systems.

In examples, a controller for an auxiliary endoscope comprises a coupling piece for attaching to a main endoscope, a handpiece connected to the coupling piece, a working shaft extending from the handpiece and extending into the coupler and a first control feature located on the handpiece for operating a pull wire extending through the working shaft, the pull wire configured to steer the auxiliary endoscope, wherein the handpiece can be moved relative to the coupling piece to adjust a position of the auxiliary scope relative to the main scope.

In examples, an endoscopy system comprises a main scope comprising a main controller, an elongate shaft extending from the main controller, the elongate shaft having a working channel extending therethough, and an access port located on the main controller to access the working channel, and an auxiliary scope comprising a slide post configured to be coupled to the access port an auxiliary controller slidably attached to the slide post an auxiliary shaft configured to extend from the auxiliary controller through the slide post and into the working channel of the main scope and a control input extending into the auxiliary controller to connect to the auxiliary shaft.

DETAILED DESCRIPTION

Figure 1:
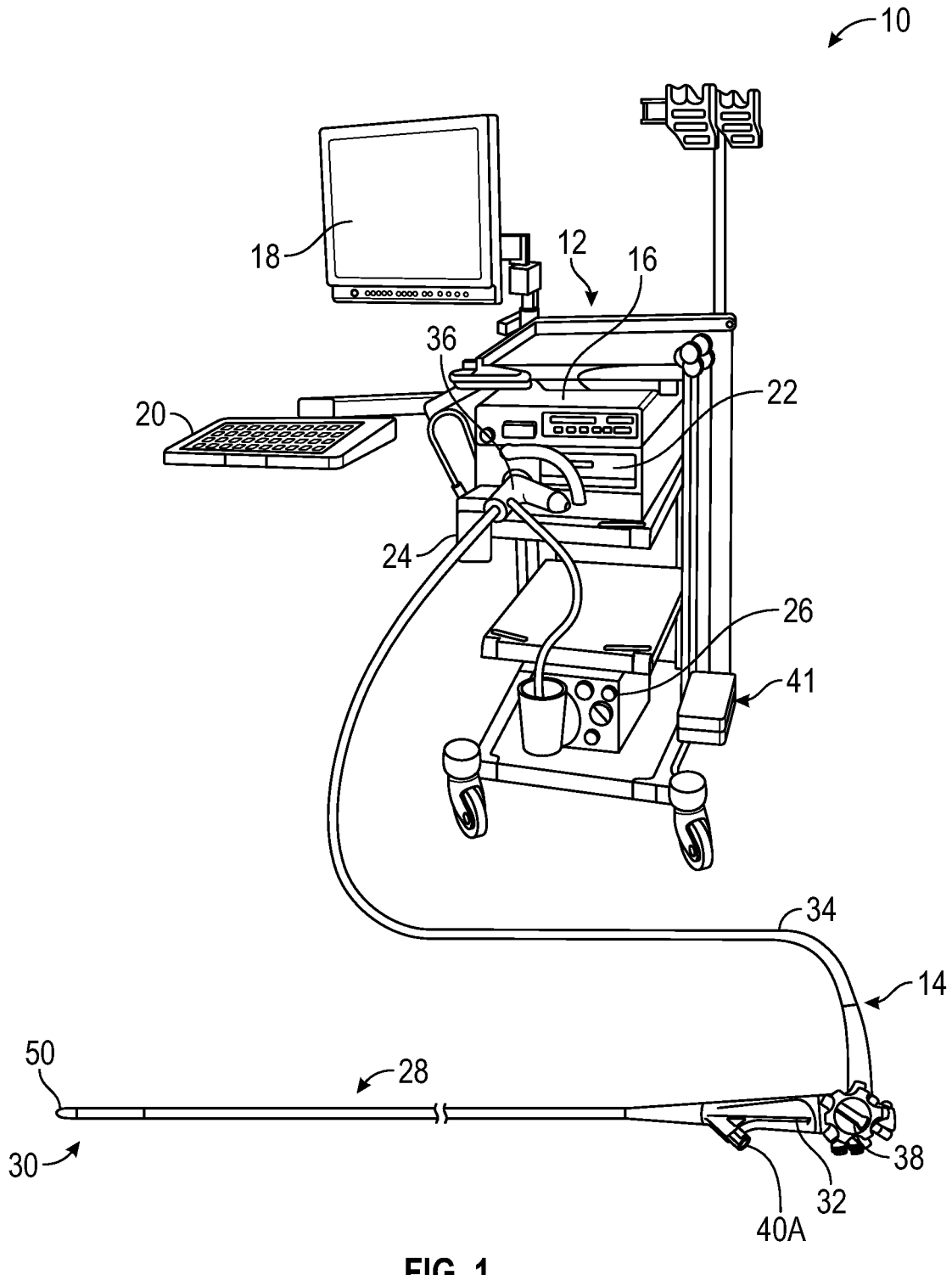
FIG. 1 is a schematic diagram of an endoscopy system comprising an imaging and control system and an endoscope, such as duodenoscope, with which the ergonomic controllers of the present disclosure can be used.

FIG. 1 is a schematic diagram of endoscopy system 10 comprising imaging and control system 12 and endoscope 14. The system of FIG. 1 is an illustrative example of an endoscopy system suitable for use with the systems, devices and methods described herein, such as ergonomic controllers. According to some examples, endoscope 14 can be insertable into an anatomical region for imaging and/or to provide passage of other devices, such as auxiliary scopes and biopsy devices or one or more therapeutic devices for treatment of a disease state associated with the anatomical region. Endoscope 14 can, in advantageous aspects, interface with and connect to imaging and control system 12. In the illustrated example, endoscope 14 comprises a duodenoscope, though other types of endoscopes can be used with the features and teachings of the present disclosure.

Imaging and control system 12 can comprise control unit 16, output unit 18, input unit 20, light source unit 22, fluid source 24 and suction pump 26.

Imaging and control system 12 can include various ports for coupling with endoscopy system 10. For example, control unit 16 can include a data input/output port for receiving data from and communicating data to endoscope 14. Light source unit 22 can include an output port for transmitting light to endoscope 14, such as via a fiber optic link. Fluid source 24 can include a port for transmitting fluid to endoscope 14. Fluid source 24 can comprise a pump and a tank of fluid or can be connected to an external tank, vessel or storage unit. Suction pump 26 can comprise a port used to draw a vacuum from endoscope 14 to generate suction, such as for withdrawing fluid from the anatomical region into which endoscope 14 is inserted. Output unit 18 and input unit 20 can be used by an operator, e.g., a user such as a surgeon or technician, of endoscopy system 10 to control functions of endoscopy system 10 and view output of endoscope 14. Control unit 16 can additionally be used to generate signals or other outputs from treating the anatomical region into which endoscope 14 is inserted. In examples, control unit 16 can generate electrical output, acoustic output, a fluid output and the like for treating the anatomical region with, for example, cauterizing, cutting, freezing and the like.

Endoscope 14 can comprise insertion section 28, functional section 30 and handle section 32, which can be coupled to cable section 34 and coupler section 36. Coupler section 36 can be connected to control unit 16 to connect to endoscope 14 to multiple features of control unit 16, such as input unit 20, light source unit 22, fluid source 24 and suction pump 26.

Insertion section 28 can extend distally from handle section 32 and cable section 34 can extend proximally from handle section 32. Insertion section 28 can be elongate and include a bending section, and a distal end to which functional section 30 can be attached. The bending section can be controllable (e.g., by control knob 38 on handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30, such as auxiliary scope 134 of FIG. 5. The working channel can extend between handle section 32 and functional section 30. Additional functionalities, such as fluid passages, guide wires, and pull wires can also be provided by insertion section 28 (e.g., via suction or irrigation passageways, wire passageways and the like).

Handle section 32 can comprise control knob 38 as well as port 40A. Control knob 38 can be coupled to a pull wire, or other actuation mechanisms, extending through insertion section 28. Port 40A, as well as other ports, such as port 40B (FIG. 2), can be configured to couple various electrical cables, guide wires, auxiliary scopes, tissue collection devices, fluid tubes and the like to handle section 32 for coupling with insertion section 28. In examples, port 40A can be used to feed an auxiliary scope or cholangioscope into insertion section 28.

Imaging and control system 12, according to examples, can be provided on a mobile platform (e.g., cart 41) with shelves for housing or supporting light source unit 22, suction pump 26, image processing unit 42 (FIG. 2), etc. Alternatively, several components of imaging and control system 12 shown in FIGS. 1 and 2 can be provided directly on endoscope 14 so as to make the endoscope "self-contained."

Functional section 30 can comprise components for treating and diagnosing anatomy of a patient. Functional section 30 can comprise an imaging device, an illumination device and an elevator, such as is described further with reference to elevator 54 of FIGS. 3A-3C.

Figure 2:
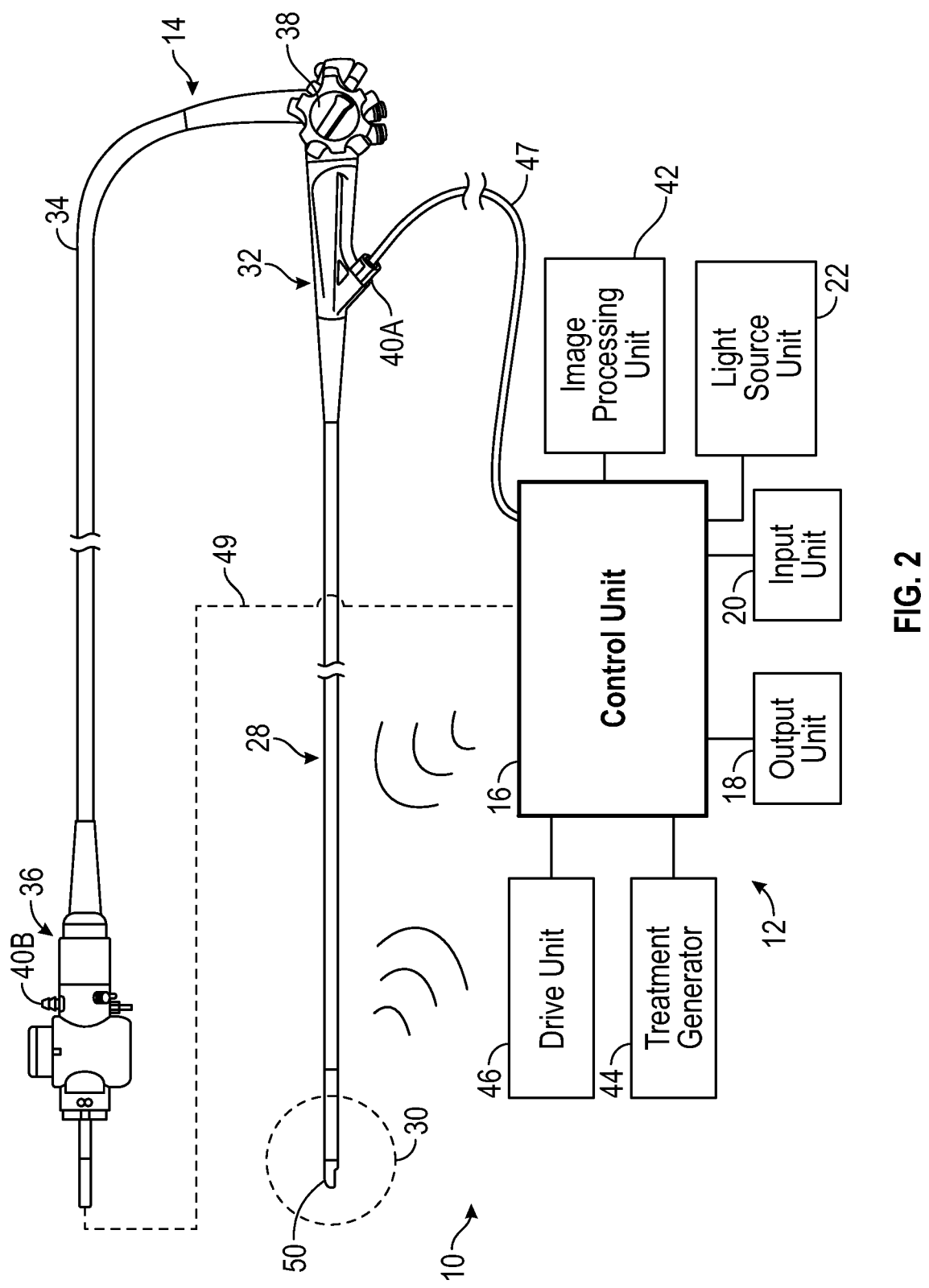
FIG. 2 is a schematic diagram of the imaging and control system of FIG. 1 showing the imaging and control system connected to the endoscope.

FIG. 2 is a schematic diagram of endoscopy system 10 of FIG. 1 comprising imaging and control system 12 and endoscope 14. FIG. 2 schematically illustrates components of imaging and control system 12 coupled to endoscope 14, which in the illustrated example comprises a duodenoscope. Imaging and control system 12 can comprise control unit 16, which can include or be coupled to image processing unit 42, treatment generator 44 and drive unit 46, as well as light source unit 22, input unit 20 and output unit 18. Coupler section 36 can be connected to control unit 16 via cable 49 (shown schematically in FIG. 2) to connect to endoscope 14 to multiple features of control unit 16, such as image processing unit 42 and treatment generator 44. In examples, port 40A can be used to insert another instrument or device, such as a daughter scope or auxiliary scope, into endoscope 14. As described herein, port 40A can be configured to couple to various attachment pieces that can support the weight of a controller for the daughter scope. Such instruments and devices can be independently connected to control unit 16 via cable 47. For example, cable 47 can comprise control input 314 of FIGS. 8A-9. In examples, port 40B can be used to connect coupler section 36 to various inputs and outputs, such as video, air, light and electric. Control unit 16 can be configured to activate a camera to view target tissue distal of endoscope 14. Likewise, control unit 16 can be configured to activate light source unit 22 to shine light on endoscope 14 or other devices extending therefrom.

Image processing unit 42 and light source unit 22 can each interface with endoscope 14 (e.g., at functional section 30) by wired or wireless electrical connections. Imaging and control system 12 can accordingly illuminate an anatomical region, collect signals representing the anatomical region, process signals representing the anatomical region, and display images representing the anatomical region on output unit 18. Imaging and control system 12 can include light source unit 22 to illuminate the anatomical region using light of desired spectrum (e.g., broadband white light, narrowband imaging using preferred electromagnetic wavelengths, and the like). Imaging and control system 12 can connect (e.g., via an endoscope connector) to endoscope 14 for signal transmission (e.g., light output from light source, video signals from imaging system in the distal end, diagnostic and sensor signals from a diagnostic device, and the like).

Fluid source 24 (FIG. 1) can be in communication with control unit 16 and can comprise one or more sources of air, saline or other fluids, as well as associated fluid pathways (e.g., air channels, irrigation channels, suction channels) and connectors (barb fittings, fluid seals, valves and the like). Fluid source 24 can be utilized as an activation energy for a biasing device or a pressure-applying device of the present disclosure. Imaging and control system 12 can also include drive unit 46, which can be an optional component. Drive unit 46 can comprise a motorized drive for advancing a distal section of endoscope 14, as described in at least PCT Pub. No. WO 2011/140118 A1 to Frassica et al., titled "Rotate-to-Advance Catheterization System," which is hereby incorporated in its entirety by this reference.

Figure 3A:
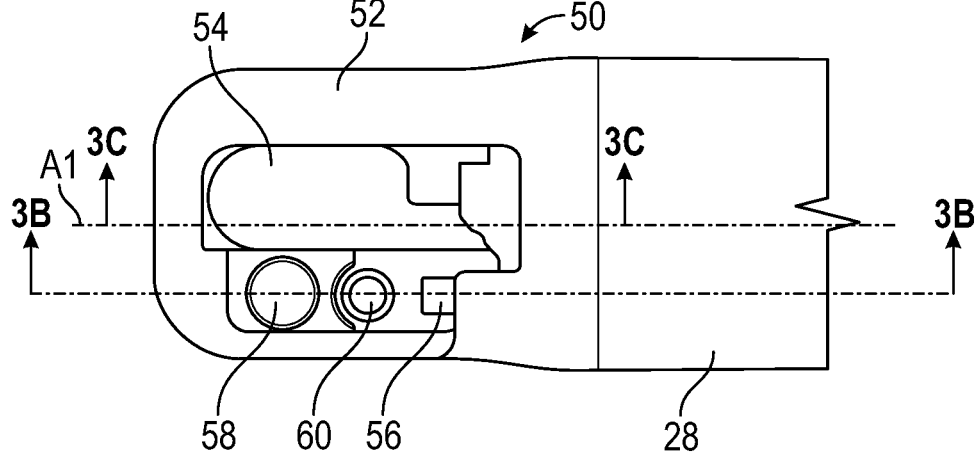
FIG. 3A is a schematic top view of a distal portion of the endoscope of FIGS. 1 and 2 comprising a camera module including optical components for a side-viewing endoscope and an elevator mechanism.
Figure 3B:
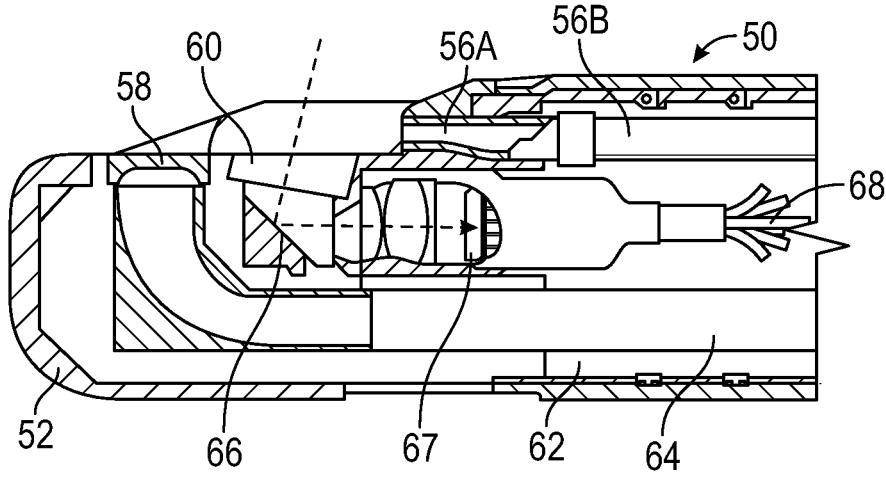
FIG. 3B is an enlarged cross-sectional view taken along the plane 3B-3B of FIG. 3A showing the optical components.
Figure 3C:
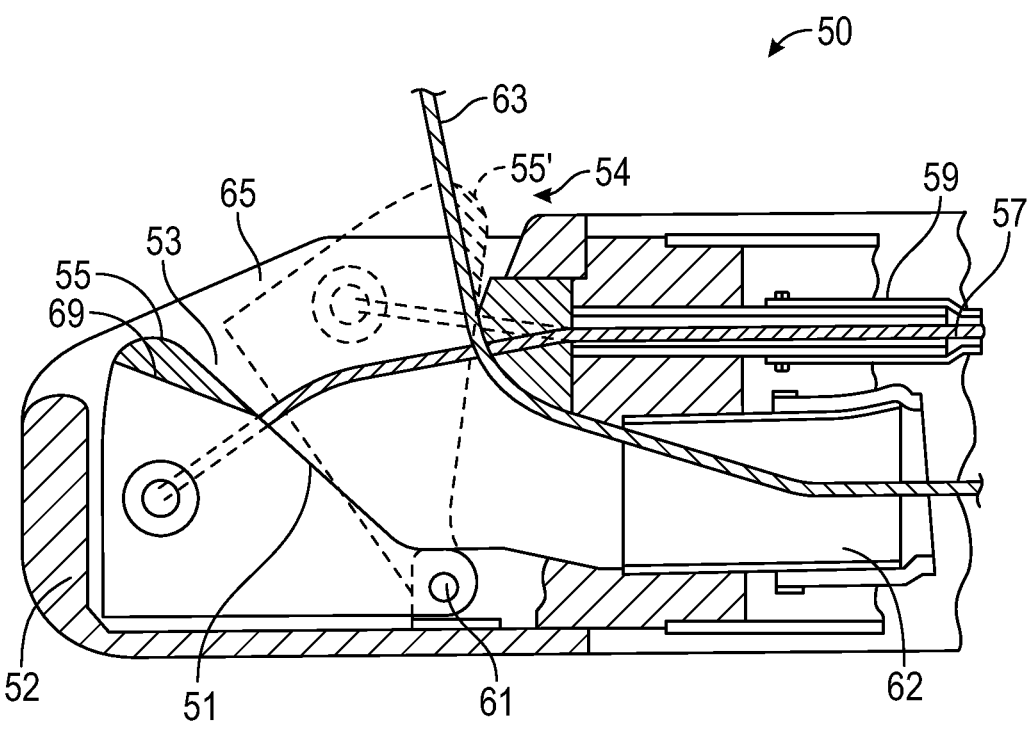
FIG. 3C is an enlarged cross-sectional view taken along the plane 3C-3C of FIG. 3A showing the elevator mechanism.

FIGS. 3A-3C illustrate a first example of functional section 30 of endoscope 14 of FIG. 2. FIG. 3A illustrates a top view of functional section 30. FIG. 3B illustrates a cross-sectional view of functional section 30 taken along section plane 3B-3B of FIG. 3A. FIG. 3C illustrates a cross-sectional view of functional section 30 taken along section plane 3C-3C of FIG. 3A. FIGS. 3A-3C illustrate side-viewing endoscope camera module 50, such as for use as a duodenoscope and the like. In side-viewing endoscope camera module 50, illumination and imaging systems are positioned such that the viewing angle of the imaging system corresponds to a target anatomy lateral to central longitudinal axis A1 of endoscope 14.

In the example of FIGS. 3A and 3B, side-viewing endoscope camera module 50 can comprise housing 52, elevator 54, fluid outlet 56, illumination lens 58 and objective lens 60. Housing 52 can form a fluid tight coupling with insertion section 28. Housing 52 can comprise opening for elevator 54. Elevator 54 can comprise a mechanism for moving a device inserted through insertion section 28, such as auxiliary scope 134 of FIG. 5. In particular, elevator 54 can comprise a device that can bend an elongate device extended through insertion section 28 along axis A1, as is discussed in greater detail with reference to FIG. 3C. Elevator 54 can be used to bend the elongate device at an angle to axis A1 to thereby treat or access the anatomical region adjacent side-viewing endoscope camera module 50. Elevator 54 is located alongside, e.g., radially outward of axis A1, illumination lens 58 and objective lens 60.

As can be seen in FIG. 3B, insertion section 28 can comprise central lumen 62 through which various components (e.g., auxiliary scope 134 of FIG. 5) can be extended to connect functional section 30 with handle section 32

(FIG. 2). For example, illumination lens 58 can be connected to light transmitter 64, which can comprise a fiber optic cable or cable bundle extending to light source unit 22 (FIG. 1). Likewise, objective lens 60 can be coupled to prism 66 and imaging unit 67, which can be coupled to wiring 68. Also, fluid outlet 56A can be coupled to fluid line 56B, which can comprise a tube extending to fluid source 24 (FIG. 1). Other elongate elements, e.g., tubes, wires, cables, can extend through central lumen 62 to connect functional section 30 with components of endoscopy system 10, such as suction pump 26 (FIG. 1) and treatment generator 44 (FIG. 2).

FIG. 3C a schematic cross-sectional view taken along section plane 3C-3C of FIG. 3A showing elevator 54. Elevator 54 can comprise deflector 55 that can be disposed in accommodation space 53 of housing 52. Deflector 55 can be connected to wire 57, which can extend through tube 59 to connect to handle section 32. Wire 57 can be actuated, such as by rotating a knob, pulling a lever, or pushing a button on handle section 32. Movement of wire 57 can cause rotation, e.g., clockwise, from a first position of deflector 55 about pin 61 to a second position of deflector 55, indicated by 55'. Deflector 55 can be actuated by wire 57 to move the distal portion of instrument 63 extending through window 65 in housing 52.

Figure 5:
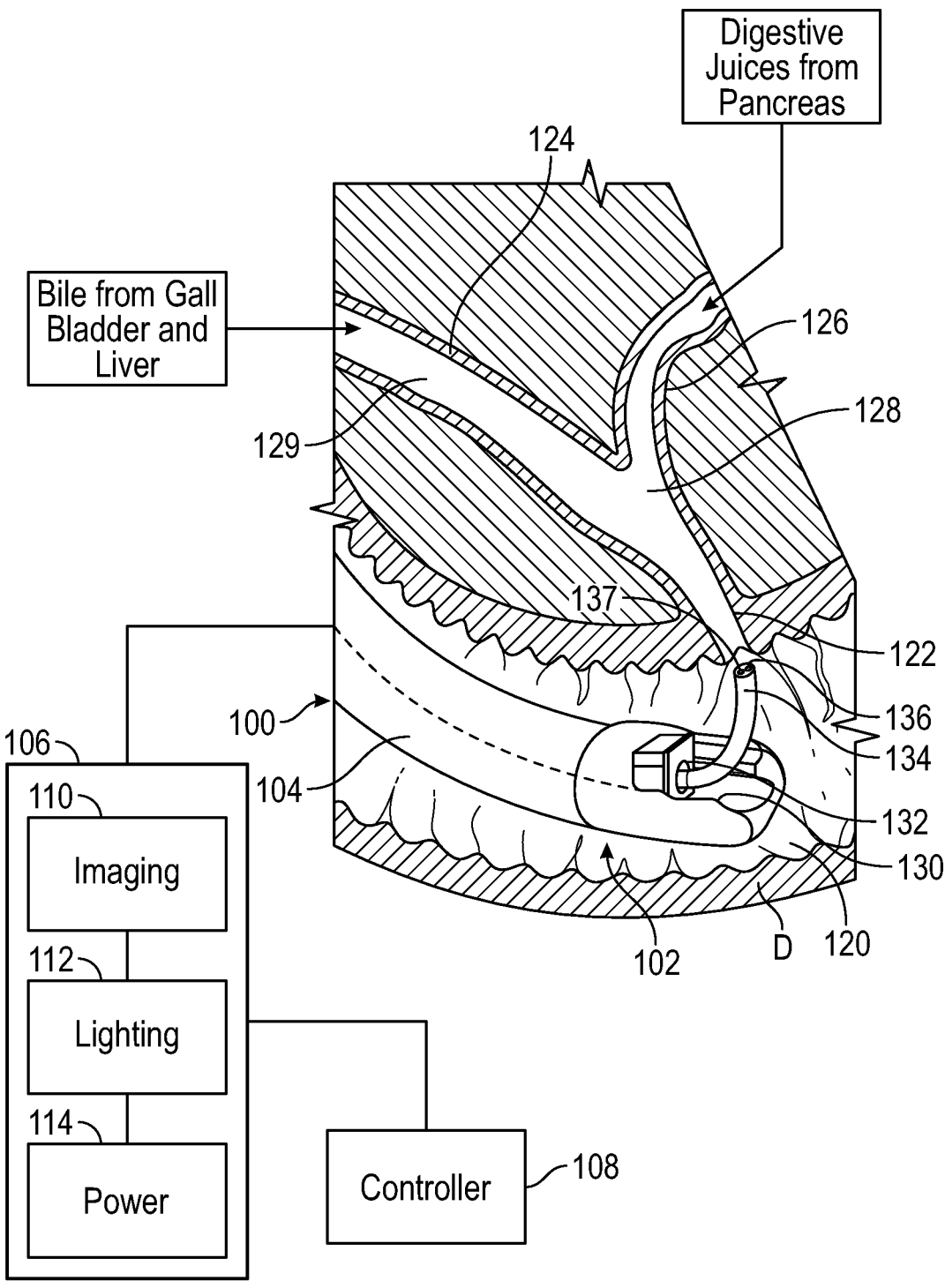
FIG. 5 is a schematic illustration of a distal portion of a duodenoscope being used to position a cholangioscope scope proximate a duodenum.

Housing 52 can comprise accommodation space 53 that houses deflector 55. Instrument 63, which is not necessarily drawn to scale in FIG. 3C, can comprise forceps, a guide wire, a catheter, or the like that extends through central lumen 62. Instrument 63 can additionally comprise auxiliary scope 134 of FIG. 5, auxiliary shaft 303 of endoscope 301 shown in FIG. 8B or a tissue collection or retrieval devices, such as those used to perform biopsies. A proximal end of deflector 55 can be attached to housing 52 at pin 61 provided to side-viewing endoscope camera module 50. A distal end of deflector 55 can be located below window 65 within housing 52 when deflector 55 is in the lowered, or un-actuated, state. The distal end of deflector 55 can at least partially extend out of window 65 when deflector 55 is raised, or actuated, by wire 57. Instrument 63 can slide on angled ramp surface 51 of deflector 55 to initially deflect the distal end of instrument 63 toward window 65. Angled ramp surface 51 can facilitate extension of the distal portion of instrument 63 extending from window 65 at a first angle relative to the axis of central lumen 62. Angled ramp surface 51 can include groove 69, e.g. a v-notch, to receive and guide instrument 63. Deflector 55 can be actuated to bend instrument 63 at a second angle relative to the axis of central lumen 62, which is closer to perpendicular that the first angle. When wire 57 is released, deflector 55 can be rotated, e.g., counter-clockwise, back to the lowered position, either by pushing or relaxing of wire 57. In examples, instrument 63 can comprise a cholangioscope or auxiliary scope 134 (FIG. 5).

Side-viewing endoscope camera module 50 of FIGS. 3A-3C can include optical components (e.g., objective lens 60, prism 66, imaging unit 67, wiring 68) for collection of image signals, lighting components (e.g., illumination lens 58, light transmitter 64) for transmission or generation of light. Side-viewing endoscope camera module 50 can also include a photosensitive element, such as a charge-coupled device ("CCD" sensor) or a complementary metal-oxide semiconductor ("CMOS") sensor. In either example, imaging unit 67 can be coupled (e.g., via wired or wireless connections) to image processing unit 42 (FIG. 2) to transmit signals from the photosensitive element representing images (e.g., video signals) to image processing unit 42, in turn to be displayed on a display such as output unit 18. In various examples, imaging and control system 12 and imaging unit 67 can be configured to provide outputs at desired resolution (e.g., at least 480p, at least 720p, at least 1080p, at least 4K UHD, etc.) suitable for endoscopy procedures.

Thus, as endoscope 14 is inserted further into the anatomy, the complexity with which it must be maneuvered and contorted increases, as described with reference to FIG. 5. Furthermore, in order to reach locations even further in the anatomy, additional devices can be used, e.g., instrument 63 in the form of auxiliary scope 134. As such, the cross-sectional area, e.g., diameter, of subsequently nested devices becomes smaller, thereby requiring even smaller devices that can be difficult to manufacture and manipulate, or satisfactorily produce results without repeated interventions (e.g., interactions with the patient). As discussed herein, the present application describes auxiliary scopes that can have full, three-hundred-sixty-degree bending capabilities by incorporating only one pull wire pair and rotational capabilities, thereby eliminating another pull wire pair to free up space for other features.

Figure 4A:
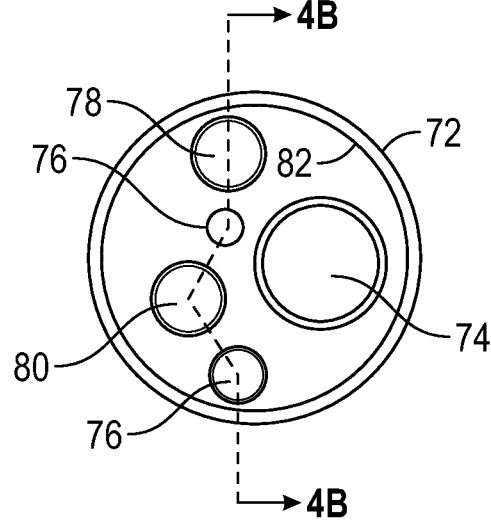
FIG. 4A is an end view of a camera module including optical and functional components suitable for use as an auxiliary scope that can be used with the endoscope of FIGS. 1 and 2.
Figure 4B:
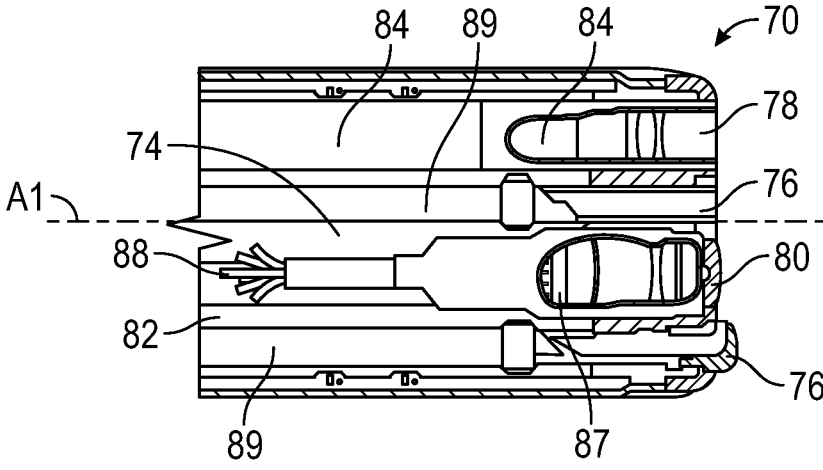
FIG. 4B is a cross-sectional view taken along section 4B-4B of FIG. 4A showing components of the camera module arranged in an end-viewing configuration.

FIG. 4A illustrates an end view of end-viewing endoscope camera module 70 and FIG. 4B illustrates a cross-sectional view of end-viewing endoscope camera module 70 taken along section plane 4B-4B of FIG. 4A. FIGS. 4A and 4B each illustrate end-viewing endoscope camera module 70, such as for use as a gastroscope, colonoscope, cholangio-scope, and the like. In end-viewing endoscope camera module 70, illumination and imaging systems are positioned such that the viewing angle of the imaging system corresponds to a target anatomy located adjacent (e.g., distal of) an end of endoscope 14 and in line with central longitudinal axis A1 of endoscope 14.

End-viewing endoscope camera module 70 of FIGS. 4A and 4B can be used as an alternative example of functional section 30 of endoscope 14 of FIGS. 1 and 2. Additionally, end-viewing endoscope camera module 70 can be used in a cholangioscope, auxiliary scope 134 of FIG. 5 and with the scope of ergonomic controller of FIGS. 6-11. For example, end-viewing endoscope camera module 70 can be located at the distal end of auxiliary shaft 303 of endoscope 301 shown in FIG. 8B or shaft 509 of FIG. 14.

In the example of FIGS. 4A and 4B, end-viewing endoscope camera module 70 can comprise housing 72, therapy unit 74, fluid outlets 76, illumination lens 78 and objective lens 80. Housing 72 can comprise and endcap for insertion section 28, thereby providing a seal to lumen 82.

As can be seen in FIG. 4B, insertion section 28 can comprise lumen 82 through which various components can be extended to connect end-viewing endoscope camera module 70 with handle section 32 (FIG. 2), for example. For example, illumination lens 78 can be connected to light transmitter 84, which can comprise a fiber optic cable or cable bundle extending to light source unit 22 (FIG. 1). Likewise, objective lens 80 can be coupled to imaging unit 87, which can be coupled to wiring 88. Also, fluid outlets 76 can be coupled to fluid lines 89, which can comprise a tube extending to fluid source 24 (FIG. 1). In examples, one of fluid outlets 76 can comprise an inlet connected to a fluid line 89 configured for suction, such as being connected to a vacuum, for recovery of lavage and irrigation fluid. Other elongate elements, e.g., tubes, wires, cables, can extend through lumen 82 to connect functional section 30 with components of endoscopy system 10, such as suction pump 26 (FIG. 1) and treatment generator 44 (FIG. 2). For example, therapy unit 74 can comprise a wide-diameter lumen for receiving other treatment components, such as cutting devices and therapeutic devices including tissue separator devices.

End-viewing endoscope camera module 70 can also include a photosensitive element, such as a charge-coupled device ("CCD" sensor) or a complementary metal-oxide semiconductor ("CMOS") sensor. In either example, imaging unit 87 can be coupled (e.g., via wired or wireless connections) to image processing unit 42 (FIG. 1) to transmit signals from the photosensitive element representing images (e.g., video signals) to image processing unit 42, in turn to be displayed on a display such as output unit 18. In various examples, imaging and control system 12 and imaging unit 87 can be configured to provide outputs at desired resolution (e.g., at least 480p, at least 720p, at least 1080p, at least 4K UHD, etc.) suitable for endoscopy procedures.

FIG. 5 is a schematic illustration of distal portion of endoscope 100 according to the present disclosure positioned in duodenum D. Endoscope 100 can comprise functional module 102, insertion section module 104, and control module 106. Control module 106 can include controller 108. Control module 106 can include other components, such as those described with reference to control unit 16 (FIG. 2). Additionally, control module 106 can comprise components for controlling a camera and a light source connected to auxiliary scope 134, such as imaging unit 110, lighting unit 112 and power unit 114. Endoscope 100 can be configured similarly as endoscope 14 of FIGS. 1 and 2.

Duodenum D can comprise duct wall 120, sphincter of Oddi 122, common bile duct 124 and main pancreatic duct 126. Duodenum D comprises an upper part of the small intestine. Common bile duct 124 carries bile from the gallbladder and liver (not illustrated) and empties the bile into the duodenum D through sphincter of Oddi 122. Main pancreatic duct 126 carries pancreatic juice from the exocrine pancreas (not illustrated) to common bile duct 124. Sometimes it can be desirable to remove biological matter, e.g., tissue, from common bile duct 124 or main pancreatic duct 126 to analyze the tissue to, for example, diagnose diseases or maladies of the patient such as cancer.

Functional module 102 can comprise elevator portion 130. Endoscope 100 can further comprise lumen 132 and auxiliary scope 134. Auxiliary scope 134 can comprise lumen 136. Auxiliary scope 134 can itself include functional components, such as camera lens 137 and a light lens (not illustrated) coupled to control module 106, to facilitate navigation of auxiliary scope 134 from endoscope 100 through the anatomy and to facilitate viewing of components extending from lumen 132. In examples, auxiliary scope 134 can include pull wires for guiding auxiliary scope 134 into sphincter of Oddi 122. In examples, auxiliary scope 134 can comprise shaft auxiliary 303 of endoscope 301 shown in FIG. 8B.

In certain duodenoscopy procedures (e.g., Endoscopic Retrograde Cholangio-Pancreatography, hereinafter "ERCP" procedures) an auxiliary scope (also referred to as daughter scope, or cholangioscope), such as auxiliary scope 134, can be attached and advanced through lumen 132 (or central lumen 62 of insertion section 28 of endoscope 14 in FIG. 3B) of the main scope (also referred to as mother scope, or duodenoscope), such as endoscope 100. Auxiliary scope 134 can be guided into sphincter of Oddi 122. Therefrom, a surgeon operating auxiliary scope 134 can navigate auxiliary scope 134 through lumen 132 toward the gall bladder, liver or other locations in the gastrointestinal system to perform various procedures. The surgeon can navigate auxiliary scope 134 past entry 128 of main pancreatic duct 126 and into passage 129 of common bile duct 124, or into entry 128. Auxiliary scope 134 can be used to guide an additional device to the anatomy to obtain biological matter, such as by passage through or attachment to lumen 136. The additional device can have its own functional devices, such as a light source, camera, tissue separators, accessories, and biopsy channel, for therapeutic procedures. As such, it can be desirable to increase the available space within auxiliary scope 134 to allow for the passage of an additional device with suitable capabilities. See, for example, intervention device 305 of FIG. 8B. According to several examples, endoscope 100 can be suitable for the removal of cancerous or pre-cancerous matter (e.g., carcinoma, sarcoma, myeloma, leukemia, lymphoma and the like), endometriosis evaluation, biliary ductal biopsies, and the like.

However, as mentioned above, the size of the additional device is typically small due to the progressively smaller sizes of endoscope 100, auxiliary scope 134 and the additional device. In examples, lumen 132 of endoscope 100 can typically be on the order of approximately 4.0 mm (0.157 inches) in diameter, while lumen 136 of auxiliary scope 134 can typically be on the order of approximately 1.2 mm (~0.05 inches). As such, with conventional devices, it can be difficult to obtain sufficiently large tissue sample sized to ensure accurate diagnoses without having to repeatedly remove and reinsert the additional device.

Figure 6:
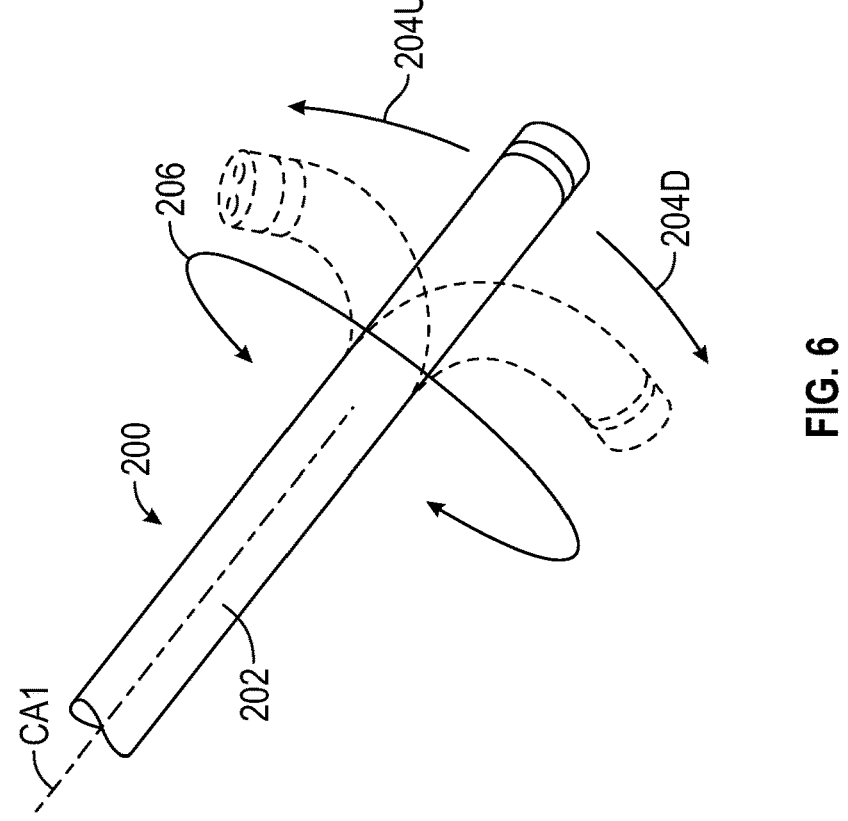
FIG. 6 is a schematic illustration of the distal end of an endoscope having two pull wires and rotational capabilities showing two-way bending and rotation relative to a central axis.

Some conventional auxiliary scopes utilize four pull wires to steer or navigate the distal tip of auxiliary scope 134 through lumen 132, into sphincter of Oddi 122 and through entry 128. As discussed, four pull wires can be operated to pull the shaft of auxiliary scope 134 in four different directions, as shown in FIG. 6, with bending in intermediary directions being achieved by puling on two pull wires simultaneously. But the presence of four pull wires occupies a large amount of the available space within the shaft of the auxiliary scope. With the present disclosure, an endoscope shaft can include two pull wires with the ability to rotate the endoscope shaft to allow the distal tip to be positioned in any radial location relative to the central axis of the endoscope shaft to facilitate steering and navigation of the shaft. Thus, the endoscope shaft can still be navigated into and through passage 129 and main pancreatic duct 126, but there can be additional working channel space to receive larger instruments or obtain larger biopsy samples, for example.

In examples, the length of auxiliary scope 134 can be sized to provide the ability to reach desired portions of common bile duct 124, main pancreatic duct 126, entry 128, and beyond. In examples, the length of auxiliary scope 134 that is desired to extend beyond the outlet of lumen 132 to reach common bile duct 124, main pancreatic duct 126 and entry 128 can be approximately ten inches (~25.4 cm) in order to provide adequate reach. In exemplary anatomy, the distance from sphincter of Oddi 122 (ampulla of Vater) to the bifurcation at entry 128 can be approximately 8 cm (~3.15 inches) and there is typically a desired to approximately advance the tip of shaft 252 an additional 4 cm (~1.6 inches) into each of common bile duct 124 and main pancreatic duct 126. As such, it can be desirable for the tip of auxiliary scope 134 to be able to extend approximately 12 centimeters (~4.7 inches) in total from the outlet of lumen 132. Also, as discussed below, the length of slide post 320 (FIG. 8A) can correspond to the length that auxiliary scope 134 is desired to extend beyond the outlet of lumen 132. In examples the length of slide post 320 can be approximately ten inches (~25.4 cm), approximately six to approximately eight inches (~15.2 cm to ~20.3 cm), or approximately 4 inches (~10.2 cm).

FIG. 6 is a schematic illustration of the distal end of endoscope 200 having two pull wires and rotational capabilities showing two-way bending and rotation relative to central axis CA1. In examples, endoscope 200 can comprise an example of auxiliary scope 134 of FIG. 5. Additionally, endoscope 200 can comprise auxiliary shaft 303 of endoscope 301 of FIG. 8B, shaft 509 of endoscope 501 of FIG. 14, shaft 609 of endoscope 601 of FIG. 15, and shaft 709 of endoscope 701 of FIG. 16A. Endoscope 200 can comprise shaft 202 in which the pull wires can be located. The pull wires can be pulled to cause, for example, upward movement shown by arrow 204U and downward movement shown by arrow 204D. Shaft 202 can additionally be rotated three-hundred-sixty degrees, as shown by arrow 206. As such, the distal tip of shaft 202 can be configured to reach various locations relative to central axis CAL such as be allowing for three-hundred-sixty-degree rotation, as discussed below. The pull wires of shaft 202 can be connected to one or more control features, such as lever 350 of FIG. 9. In examples, the control feature can be configured to simultaneously pull one pull wire while pushing the opposite pull wire.

Figure 7:
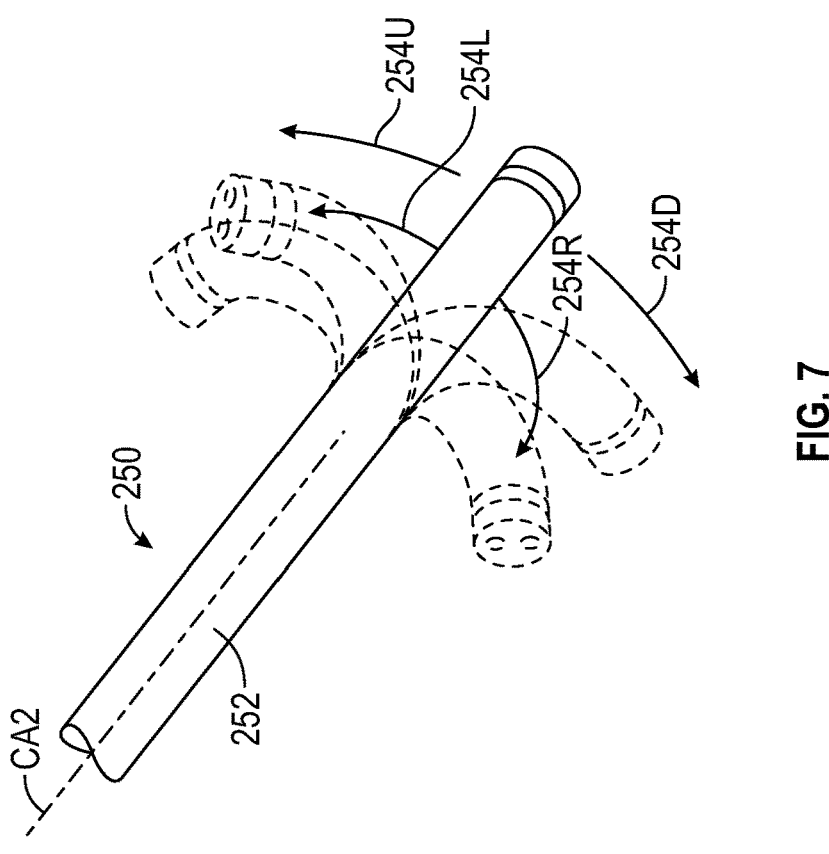
FIG. 7 is a schematic illustration of the distal end of an endoscope having four pull wires showing four-way bending relative to a central axis.

FIG. 7 is a schematic illustration of the distal end of endoscope 250 having four pull wires showing four-way bending relative to central axis CA2. In examples, endoscope 250 can comprise an example of auxiliary scope 134 of FIG. 5. Additionally, endoscope 200 can comprise auxiliary shaft 303 of endoscope 301 of FIG. 8B, shaft 509 of endoscope 501 of FIG. 14, shaft 609 of endoscope 601 of FIG. 15, and shaft 709 of endoscope 701 of FIG. 16A. Endoscope 250 can comprise shaft 252 in which the pull wires can be located. The pull wires can be pulled to cause, for example, upward movement shown by arrow 254U, downward movement shown by arrow 254D, leftward movement shown by arrow 254L and rightward movement shown by arrow 254R. The pull wires of shaft 252 can be connected to one or more control features, such as lever 350 of FIG. 9. In examples, a first control feature can be configured to simultaneously pull a first pull wire while pushing a second opposite pull wire and second control feature can be configured to simultaneously pull a third pull wire while pushing a fourth pull wire. Operation of two control features simultaneously can cause bending in intermediary directions.

Endoscope 200 of FIG. 6 and endoscope 250 of FIG. 7 can both obtain orientation of the distal tip of their respective shafts in any radial direction relative to the central axis of the shaft. However, endoscope 200 of FIG. 6 can obtain such functionality with two fewer pull wires, thereby freeing space within the endoscope as discussed herein. The rotational capabilities of endoscope 200 can be obtained in a variety of manners, including with the controllers described with reference to FIGS. 8A-16.

Figure 8A:
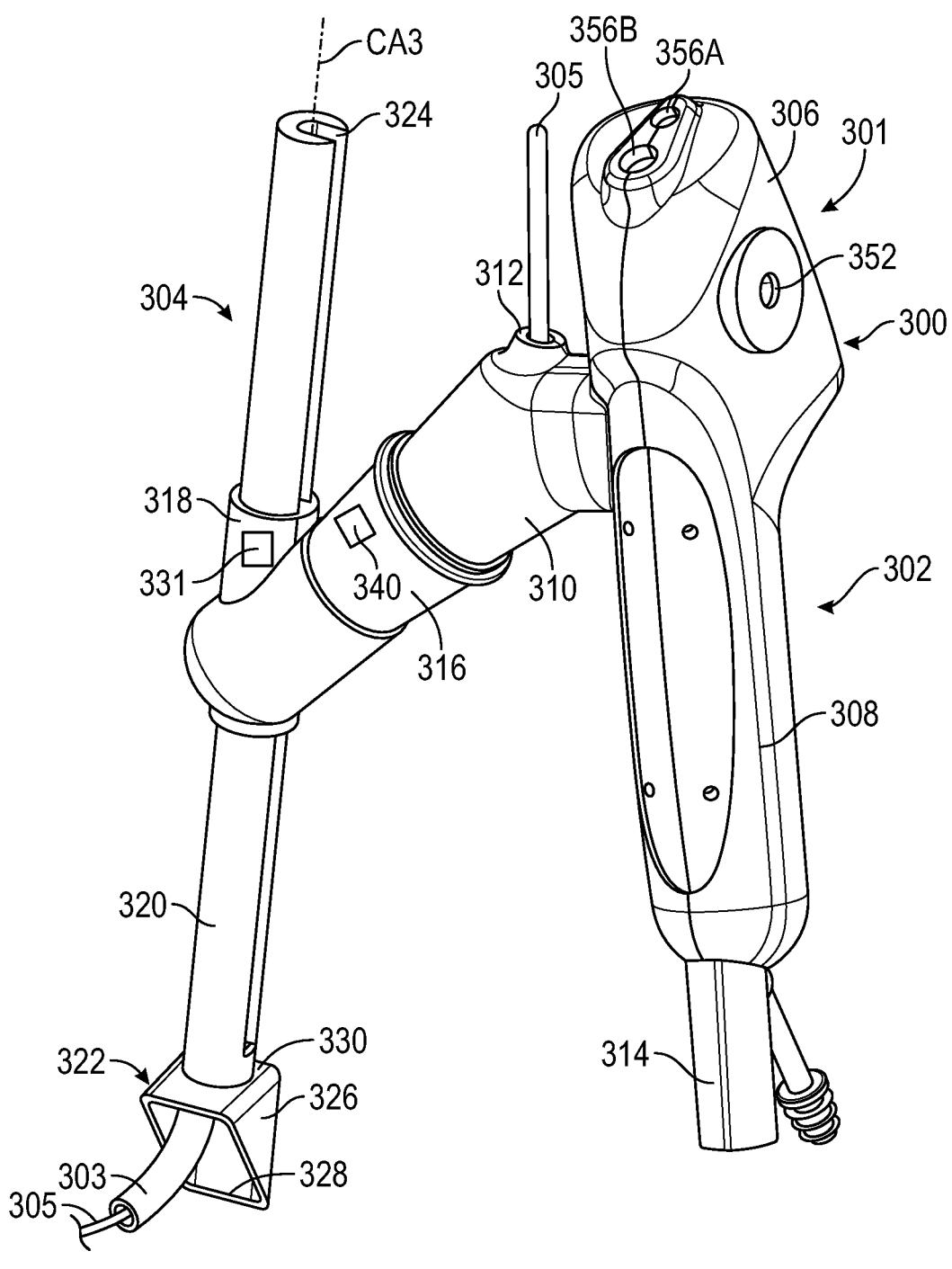
FIG. 8A is a perspective view of a controller for an endoscope according to the present disclosure having a handpiece that is pivotably attached to an attachment piece.
Figure 8B:
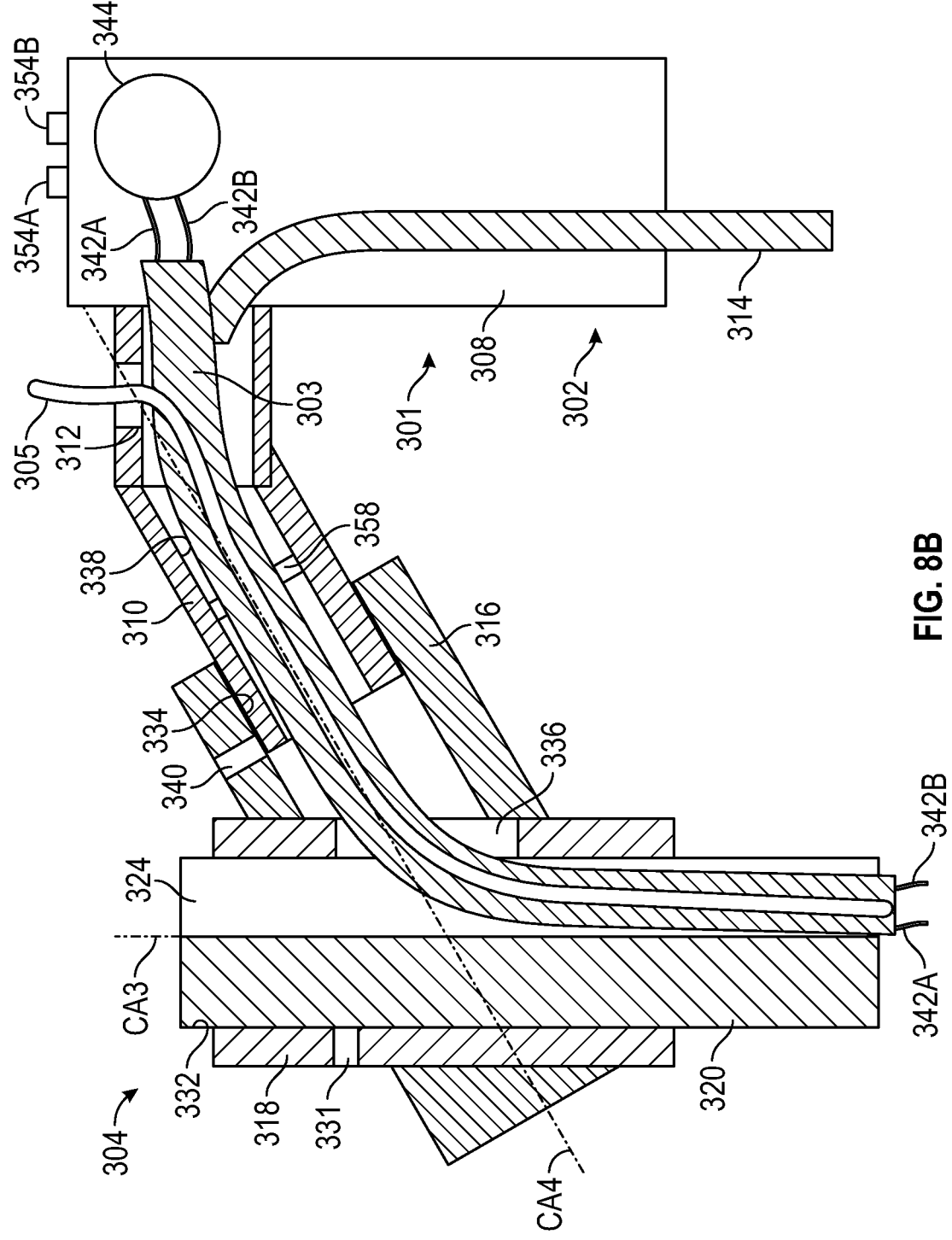
FIG. 8B is a schematic cross-sectional view of the controller of FIG. 8A showing a shaft for the endoscope extending from the handpiece through the attachment piece.

FIG. 8A is a perspective view of controller 300 for endoscope 301 according to the present disclosure comprising handpiece 302 and attachment piece 304. FIG. 8B is a schematic cross-sectional view of controller 300 of FIG. 8A showing auxiliary shaft 303 for endoscope 301 extending from handpiece 302 through attachment piece 304 and intervention device 305 extending into controller 300. FIGS. 8A and 8B are discussed concurrently.

Controller 300 can comprise handpiece 302 and attachment piece 304. Handpiece 302 can comprise control body 306, handle body 308, swivel body 310, access opening 312, and control input 314. Attachment piece 304 can comprise receiver 316, slide body 318, slide post 320 and coupler 322. In examples, controller 300 can be connected to the proximal end of shaft 202 of FIG. 6 or shaft 252 of FIG. 7. Endoscope 301 can comprise auxiliary shaft 303 and control input 314, which can be connected by controller 300.

Attachment piece 304 can comprise a coupling piece for attaching handpiece 302 to endoscope 14, a main endoscope, another scope or a duodenoscope. The attachment piece 304 can comprise one or more of receiver 316, slide body 318, slide post 320 and coupler 322. Coupler 322 can be attached to endoscope 14, such as a duodenoscope. In examples, coupler 322 can be attached to port 40A of endoscope 14 (FIG. 2). Slide post 320 can comprise a cannulated body having slot 324 into which a flexible elongate shaft of controller 300 can be inserted. Slide post 320 can extend along central axis CA3, or coupling axis or slide axis.

Coupler 322 can be attached to a duodenoscope using various means, such as couplers, fasteners, hook and loop material, a threaded collar, set screws, adhesive and the like. In examples, coupler 322 can comprise housing 326 having opening 328. Housing 326 can be positioned over port 40A of handle section 32 (FIG. 2). Housing 326 can have a shape that mates with the shape of a port on a handle of a duodenoscope such that housing 326 can be fit onto the port with an interference fit, that can fit over the port and be immobilized using fasteners, or other means. For example, the inner perimeter of opening 328 can be slightly larger than the outer perimeter of a port on the duodenoscope. In examples, opening 328 can have rectilinear profiles, such as square or rectangular, or curved profiles, such as circular or oval.

Slide post 320 can extend from coupler 322 along central axis CA3. Slide post 320 can comprise an elongate rigid body that can be maintained in a fixed position relative to coupler 322. In examples, slide post 320 can be made of rigid plastic or metal. In additional examples, slide post 320 can be made of a flexible tube, such as a gooseneck tube. Slide post can have sufficient strength due to, for example, thickness and material properties, to support handpiece 302. Slide post 320 can include an internal passage or lumen to allow for passage of components therethrough, such as the shaft of a cholangioscope extending from controller 300. Slot 324 can extend along all or portions of slide post 320 and can penetrate into the internal passage or lumen. In examples, slot 324 can extend from coupler 322 at a distal end to a location closer to the opposite, proximal end. In examples, slot 324 can extend the length of slide post 320. Housing 326 can include opening 330 to which slide post 320 can be joined.

Slide body 318 can comprise an annular body configured to slide on slide post 320 along axis CA3. In examples, slide body 318 can be held in place on slide post 320 via friction. In examples, slide body 318 can include lock button 331. Lock button 331 can be configured to prevent relative movement of slide body 318 relative to slide post 320. For example, lock button 331 can be configured to have an internal surface to press against slide post 320 to prevent movement via friction. In examples, lock button 331 can be configured to have internal teeth that mate with notches or grooves (not visible in the figure views) positioned along the length of slide post 320. In examples, lock button 331 can be spring loaded so as to be biased to an unlocked position. An operator can depress lock button 331 to overcome the spring force and temporarily prevent movement of slide body 318 relative to slide post 320. In examples, slide body 318 and slide post 320 can include mating rails and grooves (not visible in the figure views) extending parallel to axis CA3 to prevent rotation of slide body 318 about axis CA3 so that only linear translational movement is permitted. For example, slide body 318 can include a tab or flange that rides in slot 324 to prevent relative rotation between slide body 318 and slide post 320.

Receiver 316 can receive swivel body 310. Receiver 316 and swivel body 310 can extend along axis CA4, or handpiece axis or swivel axis, as best seen in FIG. 8B. In examples, internal surface 334 can comprise a circular surface to receive a mating circular surface of swivel body 310. Swivel body 310 can comprise a component of handpiece 302 that conveys or transfers internal components of control body 306 and handle body 308 to attachment piece 304 via internal passage 338. Swivel body 310 can be configured to rotate within receiver 316. In examples, swivel body 310 can be held in place within receiver 316 by friction. In examples, receiver 316 can include lock button 340. As with lock button 331, lock button 340 can be spring activated and can be configured to apply frictional force to swivel body 310 to prevent relative rotation. Lock button 340 can have additional configurations, such as by being configured to have a detent that mates with notches or grooves in swivel body 310.

Slide body 318 can include internal surface 332 (FIG. 8B) to engage slide post 320. Slide body 318 can be connected to receiver 316, which can comprise an annular body configured to receive swivel body 310. Receiver 316 can comprise internal surface 334 (FIG. 8B) to engage swivel body 310. Slide body 318 can include aperture 336 (FIG. 8B) to connect slot 324 with the lumen of receiver 316 formed by internal surface 334. Swivel body 310 can comprise internal passage 338 (FIG. 8B) to allow passage between receiver 316 and handle body 308. As such, a continuous opening can be formed from internal surface 334, aperture 336, slot 324, opening 330 and housing 326. Such a passage can allow for the insertion of auxiliary shaft 303 of controller 300 through attachment piece 304.

Auxiliary shaft 303 can comprise a flexible elongate shaft, such as shaft 202 of FIG. 6, and can be connected to handpiece 302 and can extend through swivel body 310, receiver 316, slide post 320 and into coupler 322. As discussed, coupler 322 can connect to an access opening for the working channel of a duodenoscope. Pull wires 342A and 342B can extend into auxiliary shaft 303 and extend therethrough to the distal end of auxiliary shaft 303. Pull wires 342A and 342B can connect to actuator 344 in handle body 308. Actuator 344 can comprise a drum or barrel that can attach to pull wires 342A and 342B. Actuator 344 can connect to lever 350 (FIG. 9), such as via a rod or shaft extending through aperture 352 (FIG. 8A) in control body 306.

Control input 314 can extend into auxiliary shaft 303 to provide functionality to the distal end of auxiliary shaft 303. Control input 314 can comprise tubes, hoses or cables that can connect to a controller, such as control unit 16 (FIGS. 1 and 2). Control input 314 can include passages for conveying fluid, such as water or air, electrical signals, such as for operating illumination and imaging capabilities of endoscope 301, and treatment energy, such as electricity, ultrasound, ablation, cryogenic and the like. In examples, control input 314 can comprise fluid tube 315A and power cable 315B. Control input 314 can connect to buttons 354A and 354B (FIG. 8B) for operating the capabilities of endoscope 301. Buttons 354A and 354B can connect to control input 314 via appropriate wiring or cable (not illustrated) extending through apertures 356A and 356B in control body 306. Buttons 354A and 354B can be configured to operate valves or switches to allow fluid or electricity to flow from control input 314 to auxiliary shaft 303.

Intervention device 305, such as a catheter, needle, biopsy device or tissue retrieval device, can be inserted into access opening 312 and extended into the flexible elongate shaft to reach the working channel of the duodenoscope to which controller 300 is attached. In examples, access opening 312 can be located on the top of controller 300, such as on a proximal surface of swivel body 310. However, access opening 312 can be positioned in other locations, such as on handle body 308. Intervention device 305, once inserted into access opening 312, can remain in a fixed axial position relative to auxiliary shaft 303 of controller 300. For example, auxiliary shaft 303 can be attached or anchored to swivel body 310 via brace 358. In examples, brace 358 can comprise a flexible disk having a central aperture in which auxiliary shaft 303 can be positioned at an outer perimeter attached to swivel body 310, such as via adhesive, or fasteners. Thus, rotational movement of swivel body 310 relative to receiver 316 can additionally result in rotation of auxiliary shaft 303 relative to receiver 316. Likewise, movement of swivel body 310 relative to slide post 320 can additionally result in movement of auxiliary shaft 303 relative to axis CA3. Auxiliary shaft 303 can additionally or alternatively be secured to swivel body 310 by other means, such as fasteners, adhesives, hook and loop fastener material and the like.

Figure 10:
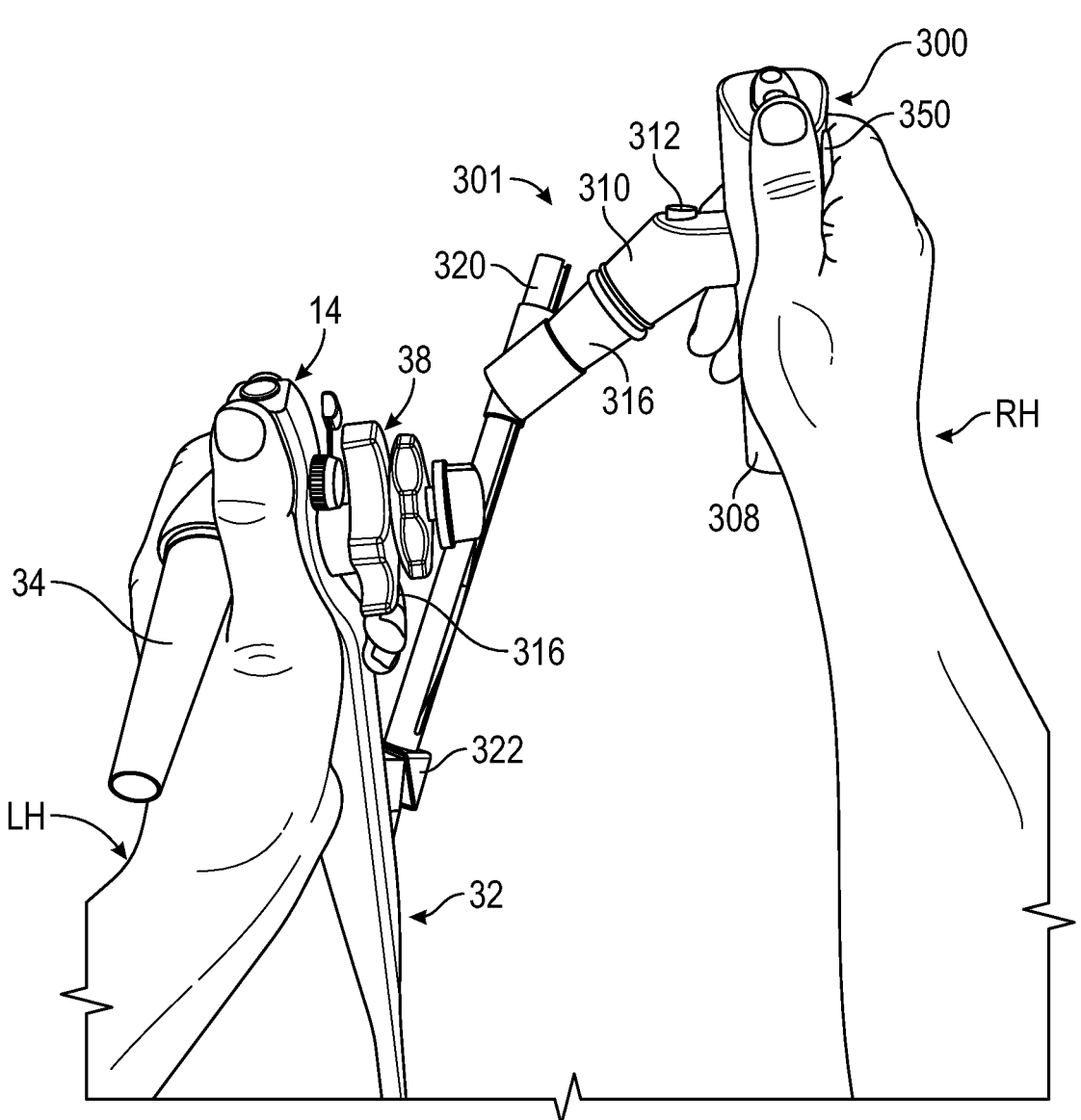
FIG. 10 is a perspective view of the controller of FIGS. 8A and 9 as held by an operator when connected to a duodenoscope.
Figure 11:
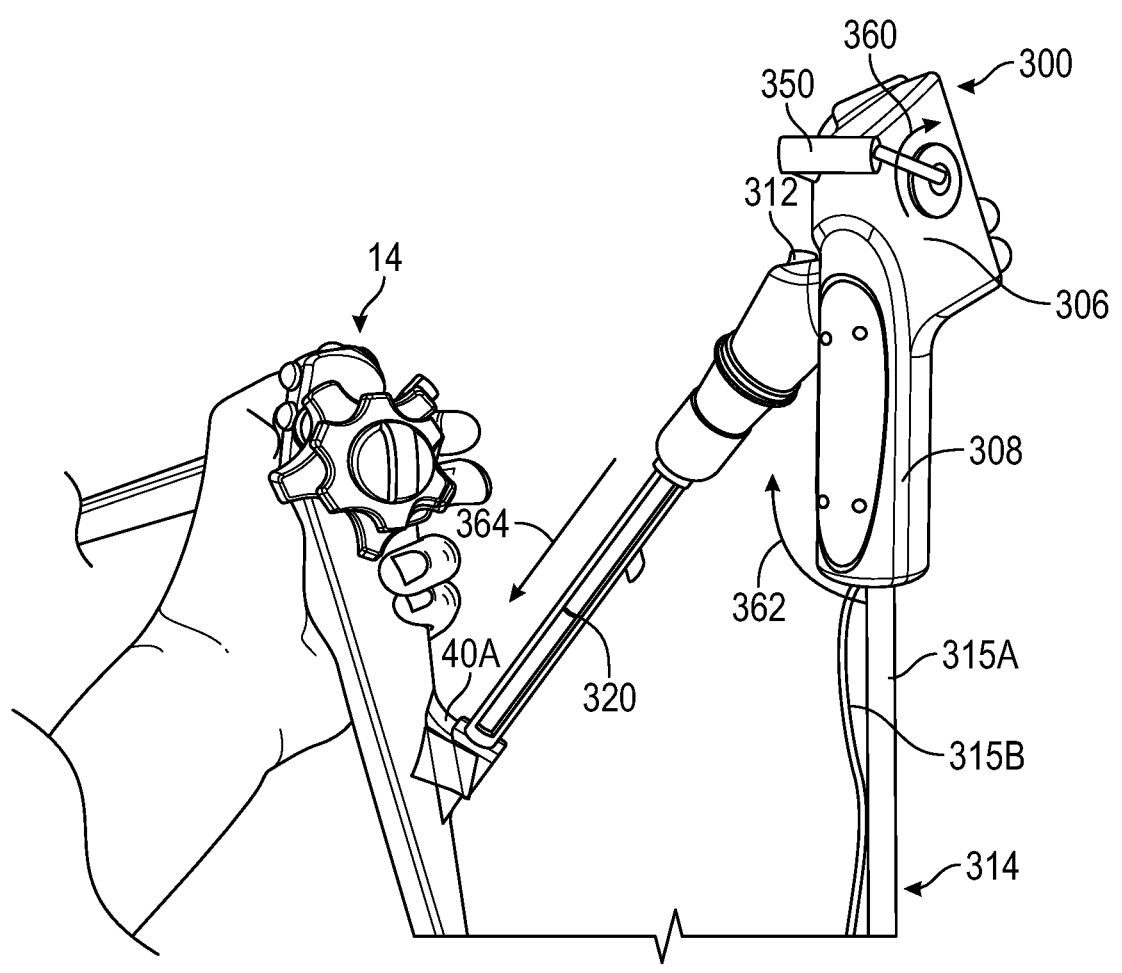
FIG. 11 is a diagram illustrating the controller of FIG. 10 with various control motions illustrated.

Configured as such, handle body 308 can be supported relative to slide post 320 by receiver 316 and swivel body 310. Thus, with slide post 320 attached to a mother scope or duodenoscope via coupler 322, handle body 308 can be supported relative to the mother scope in an ergonomic position, as shown in FIGS. 10 and 11. Movements of handle body 308 can be executed by an operator using one hand, such as a right hand, to axial advance and retreat, rotate and bend auxiliary shaft 303. As discussed below, rotation of handle body 308 along axis CA4 can cause rotation of auxiliary shaft 303 within the mother scope, raising and lowering of handle body 308 along slide post 320 can cause retreating and advancing of auxiliary shaft 303 within the mother scope, and actuation of actuator 344 (FIG. 9) can cause bending of the distal tip of auxiliary shaft 303 relative to the mother scope.

Figure 9:
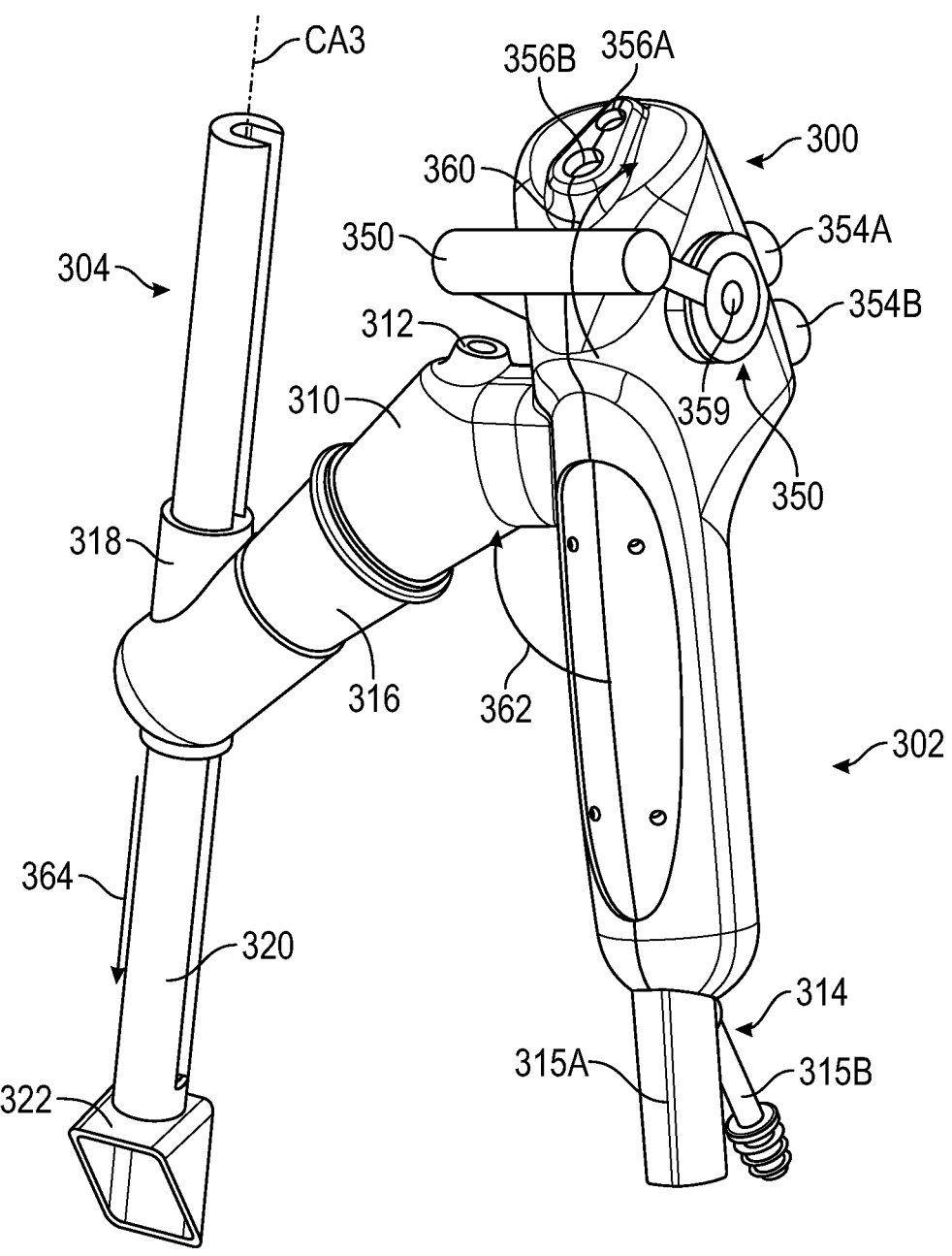
FIG. 9 is a perspective view of the controller of FIG. 8A showing various control motions of the controller.

FIG. 9 is a perspective view of controller 300 of FIG. 8A showing various control motions of controller 300. Lever 350 can be attached to handle body 308 of handpiece 302 at aperture 352 (FIG. 8A) and to pull wires 342A and 342B (FIG. 8B). Additionally, buttons 354A and 354B can be attached to handle body 308 at apertures 356A and 356B (FIG. 8A), respectively, to operate features of control input 314.

Lever 350 can be actuated by an operator to move pull wires within auxiliary shaft 303. Lever 350 can be connected to actuator 344 to cause rotation thereof. For example, lever 350 can be moved up and down as shown by arrow 360. In examples, upward movement of lever 350 can cause upward movement of auxiliary shaft 303, similar to what is indicated by arrow 204U in FIG. 6 relative to shaft 202, and downward movement of lever 350 can cause downward movement of auxiliary shaft 303, similar to what is indicated by arrow 204D in FIG. 6 relative to shaft 202. In examples, lever 350 can be provided with lock button 359. Lock button 359 can be configured similarly as other lock buttons described herein to immobilize lever 350 relative to handle body 308. In examples, lever 350 can be motorized. Buttons for controlling motors for lever 350 can be included on handpiece 302, on a clip-on device for a duodenoscope, or on a foot pedal. For example, a motor can be positioned on or in handle body 308 along the axis of rotation for lever 350, the motor can be connected to a power source, such as from imaging and control system 12 (FIG. 1) and another button or switch on handle body 308 or a tethered device that can be attached to a duodenoscope or a foot pedal. In examples, drive unit 46 (FIG. 2) can include a motor that can rotate a flexible drive shaft that can be extended to lever 350 through control input 314 to provide power input to any of the control features described herein such as to provide pull wire actuation or working shaft rotation. As such, controls for lever 350 can be positioned remotely from handpiece 302 in more convenient or ergonomic positions for use by an operator, such as via foot operation. As such, other operations of handpiece 302 can be more freely performed by an operator without having to have a hand in position to operate lever 350.

Rotation can be applied to handpiece 302 at handle body 308 as indicated by arrow 362. Motion of handpiece 302 indicated by arrow 362 can cause swivel body 310 to rotate within receiver 316 along axis CA4. In examples, upward motion of handle body 308 can cause rotation of auxiliary shaft 303, similar to what is indicated by arrow 206 in FIG. 6 in a clockwise rotation about central axis CA1 relative to shaft 202, and downward motion of handle body 308 can cause rotation of auxiliary shaft 303, similar to what is indicated by arrow 206 in FIG. 6 in a counter-clockwise rotation about central axis CA1 relative to shaft 202.

Linear movement can be applied to handpiece 302 at handle body 308 as indicated by arrow 364. Motion of handpiece 302 indicated by arrow 364 can cause swivel body 310 to push and pull receiver 316 along slide post 320. In examples, upward motion of handle body 308 can cause translation of auxiliary shaft 303 backward with respect to a distal tip of endoscope 14, and downward motion of handle body 308 can cause translation of auxiliary shaft 303 forward with respect to the distal tip of endoscope 14, as discussed in greater detail with reference to FIGS. 10-12C.

FIG. 10 is a perspective view of controller 300 of FIGS. 8A and 9 as held by an operator. In the example of FIG. 10, left hand LH of the operator can grasp handle section 32 of endoscope 14 and right hand RH of the operator can grasp handle body 308 of endoscope 301. In examples, as can be seen in FIG. 10, slide post 320, receiver 316 and swivel body 310 can be configured to hold handle body 308 generally parallel to endoscope 14. That is an axis extending through the major dimension of handle body 308 can extend generally parallel to an axis extending through the major dimension of handle section 32. Such a position provide an ergonomically comfortable position for right hand RH relative to left hand LH and allows for instinctive manipulation of controller 300 relative to handle section 32.

The weight of both endoscope 14 and endoscope 301 can be supported by both left hand LH and right hand RH. Left hand LH can be used to operate endoscope 14 in a customary fashion. Left hand LH can be held steady to provide resistance for the operation of endoscope 301 with right hand RH. That is, left hand LH can support endoscope 14 to resist twisting of handle body 308 at receiver 316 and translation of handle body 308 along slide post 320.

Right hand RH can be moved downward relative to FIG. 10 to slide receiver 316 downward along slide post 320 toward endoscope 14, and right hand RH can be moved upward relative to FIG. 10 to slide receiver 316 upward along slide post 320 away from endoscope 14. See arrow 364 of FIG. 11.

The wrist of right hand RH can be flexed to twist handle body 308 relative to receiver 316. For example, the wrist of right hand RH can be flexed forward relative to FIG. 10 in an ulnar deviation to produce clock-wise rotation of auxiliary shaft 303 (looking down the length of slide post 320 toward endoscope 14), and the wrist of right hand RH can be flexed backward relative to FIG. 10 in a radial deviation to produce counter-clock-wise rotation of auxiliary shaft 303 (looking down the length of slide post 320 toward endoscope 14). See arrow 362 of FIG. 11.

The thumb of right hand RH can be moved upward relative to FIG. 10 to push lever 350 (FIG. 12A) upward, and the thumb of right hand RH can be moved downward relative to FIG. 10 to push lever 350 (FIG. 12A) downward. See arrow 360 of FIG. 11.

Figures 12A, 12B, 12C:
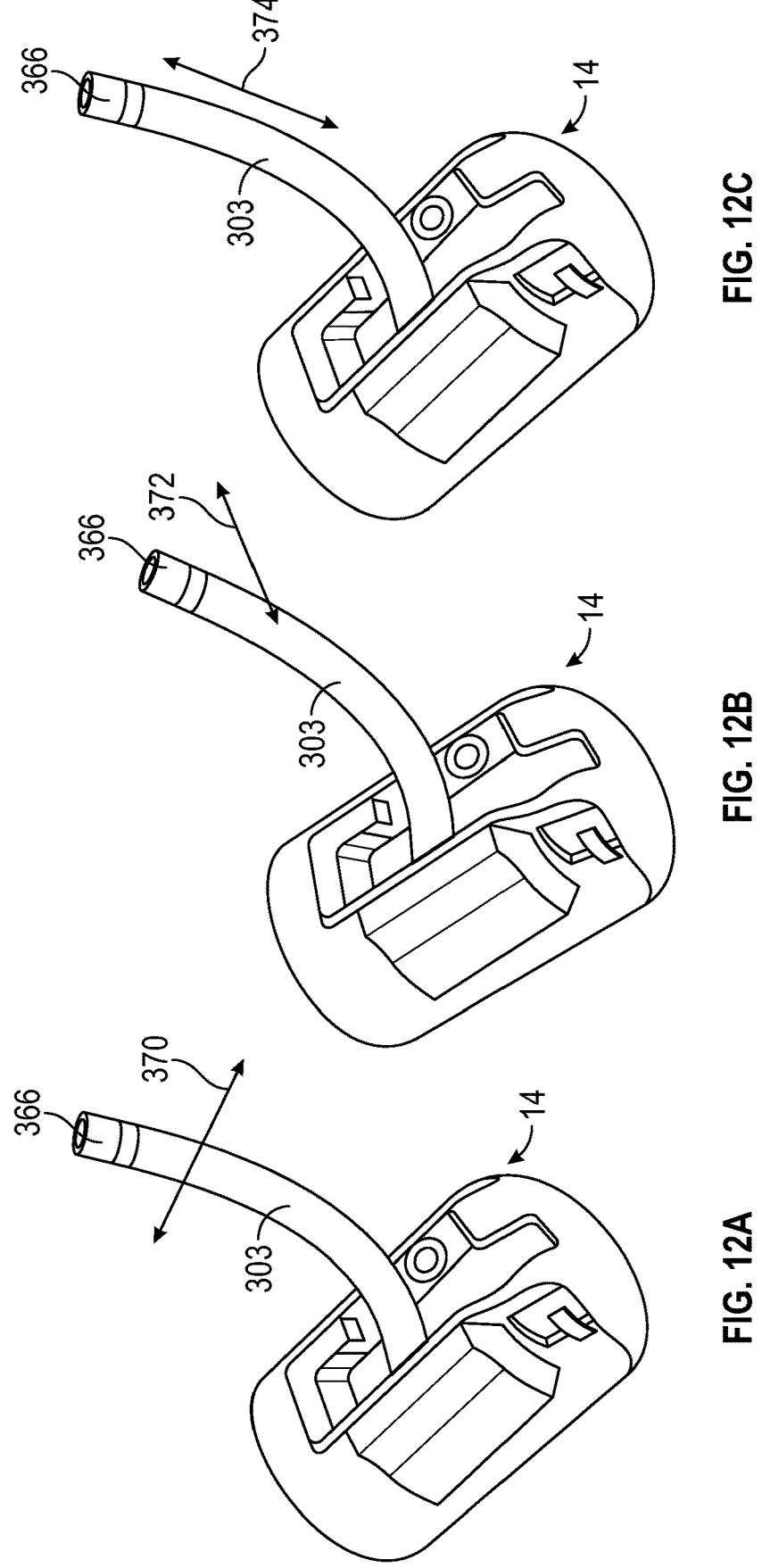
FIG. 12A is a schematic illustration of a distal tip of an endoscope attached to the controller of FIG. 11 in a first state showing bending of the distal tip.
FIG. 12B is a schematic illustration of a distal tip of an endoscope attached to the controller of FIG. 11 in a second state showing rotation of the distal tip.
FIG. 12C is a schematic illustration of a distal tip of an endoscope attached to the controller of FIG. 11 in a third state showing extension of the distal tip.

As described with reference to FIGS. 11-12C, movements of right hand RH can cause control movements of controller 300 that result in movements of distal tip 366 (FIGS. 12A-12C) of auxiliary shaft 303.

FIG. 11 is a diagram illustrating controller 300 of FIG. 10 with various control motions illustrated by arrows 360, 362 and 364 to induce movements of distal tip 366 illustrated by arrow 370 (FIG. 12A), arrow 372 (FIG. 12B) and arrow 374 (FIG. 12C), respectively.

Movement of lever 350 along the direction of arrow 360 can result in movement, e.g., radial bending, of distal tip of auxiliary shaft 303 in the direction of arrow 370. Lever 350 can pull on pull wires 342A and 342B (FIG. 8B) extending through auxiliary shaft 303 to bend the distal tip of auxiliary shaft 303.

Movement of handle body 308 along the direction of arrow 362 can result in movement, e.g., rotation, of distal tip of auxiliary shaft 303 in the direction of arrow 372. Rotation of handle body 308 can cause auxiliary shaft 303 to twist within slide post 320 and endoscope 14.

Movement of handle body 308 along the direction of arrow 364 can result in movement, e.g., axial translation, of the distal tip of auxiliary shaft 303 in the direction of arrow 374. Pushing and pulling of handle body 308 can push and pull auxiliary shaft 303 within slide post 320 and endoscope 14.

As described herein, attachment piece 304 of FIGS. 8A-12C can provide a support for controller handpiece 302 on another scope, such as a duodenoscope. Thus, an operator need not always have a hand on controller 300 to maintain controller 300 in a convenient location for using. Slide post 320, receiver 316 and swivel body 310 can position handpiece 302 relative to the other scope that is comfortable for the operator to reduce fatigue and repetitive stress injuries. Additionally, handpiece 302 can be joined to attachment piece 304 in such a way that operation of endoscope 301 is simplified, such as allowing a movement of handpiece 302 relative to attachment piece 304 to control a movement of auxiliary shaft 303. Additionally, control features for operating endoscope 301, including pull wires and treatment operations, can be located on handpiece 302 in ergonomic positions. In examples, a hand placed on handpiece 302 can perform all movements of auxiliary shaft 303 (i.e., axial movement, radial bending and rotation) and control all operations of endoscope 301 (irrigation, treatment energy, imaging, etc.) without having to reposition the hand.

Figure 13:
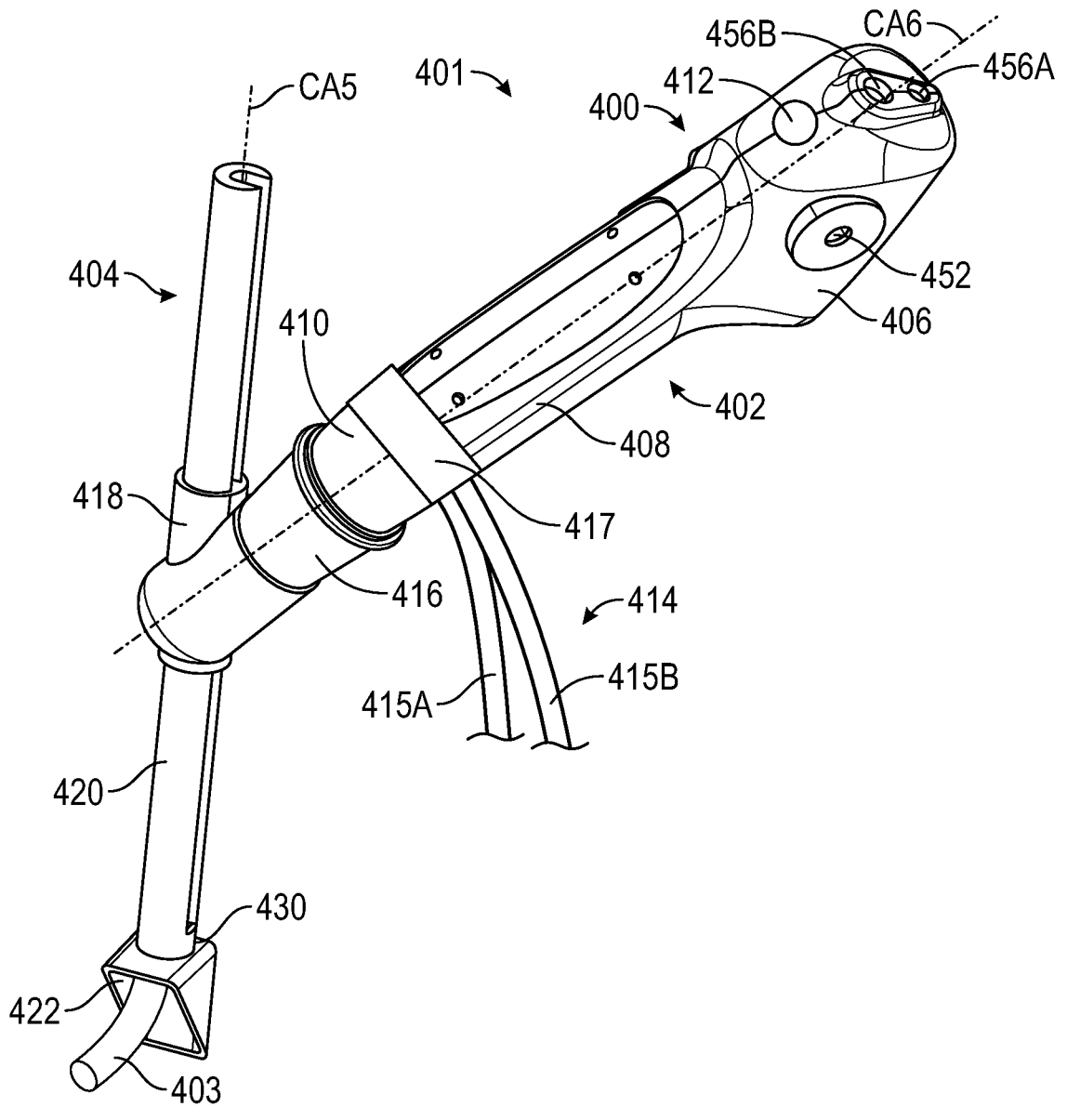
FIG. 13 is a schematic illustration of a controller for an endoscope wherein the handpiece is rotatable within the attachment piece to facilitate three-hundred-sixty degree rotation.

FIG. 13 is a schematic illustration of controller 400 for auxiliary scope 401. In examples, auxiliary scope 401 can comprise auxiliary scope 134 of FIG. 5. Controller 400 can comprise handpiece 402 and attachment piece 404. In examples, controller 400 can be connected to the proximal end of shaft 202 of FIG. 6 or shaft 252 of FIG. 7.

Handpiece 402 can comprise control body 406, handle body 408, swivel body 410, access opening 412. Handpiece 402 can be connected to shaft 403 and control input 414.

Attachment piece 404 can comprise receiver 416, slide body 418, slide post 420 and coupler 422 having opening 430. Attachment piece 404 can be configured similarly as attachment piece 304 of FIGS. 8A-11.

Control body 406 and handle body 408 can be configured similarly as control body 306 and handle body 308 of FIGS. 8A-11. However, swivel body 310 of controller 300 can be replaced by swivel body 410, which can be configured to allow control body 406 and handle body 408 to rotate more easily about axis CA6 in a three-hundred-sixty-degree manner. That is, the axis of handle body 408 can align with the axis of receiver 416. As with the examples of FIGS. 8A-12C, the axis of handle body 408 can be oblique to axis CA6. Thus, operation of controller 400 can be similar to operation of controller 300 except for the ergonomic arrangement of handle body 408 relative to receiver 416 and the inclusion of swivel ring 417.

In examples, slide body 418 can be held in place on slide post 420 via friction. In examples, slide body 418 can include a lock button similar to lock button 331 of FIG. 8A. In examples, receiver 416 can include a lock button similar to lock button 340 of FIG. 8A.

Control input 414 can comprise fluid tube 415A and power cable 415B, which can be attached to controller 400 through swivel ring 417. Swivel ring 417 can allow control input 414 to remain stationary while control body 406 and handle body 408 rotate about axis CA6. In examples, handle body 408 and swivel body 410 can be rigidly connected and extend through swivel ring 417. Thus, rotation of handle body 408 can produce rotation of swivel body 410 within both of swivel ring 417 and receiver 416. However, swivel ring 417 can remain stationary to avoid control input 414 from having to rotate about axis CA6. The interior of swivel ring 417 can include fluid and electrical couplers for providing outputs of fluid tube 415A and power cable 415B to shaft 403, such as rotary unions.

Control body 406 can include apertures 456A and 456B for receiving buttons to operate control input 414. Control body 406 can also include aperture 452 for receiving an actuator for operating pull wires extending into shaft 403. Access opening 412 can be used to feed another instrument, such as intervention device 305 (FIG. 8A) into shaft 403.

The example of FIG. 13 can allow an operator to provide multiple rotational inputs to handle body 408 along axis CA6 to, if desired, completely rotate handle body 408 and shaft 403 about axis CA6, without interference from control input 414. Thus, the distal tip of shaft 403 can be readily positioned in any orientation relative to axis CA6 when the pull wires are actuated to facilitate ease of shaft 403 reaching desired locations within the anatomy.

Figure 14:
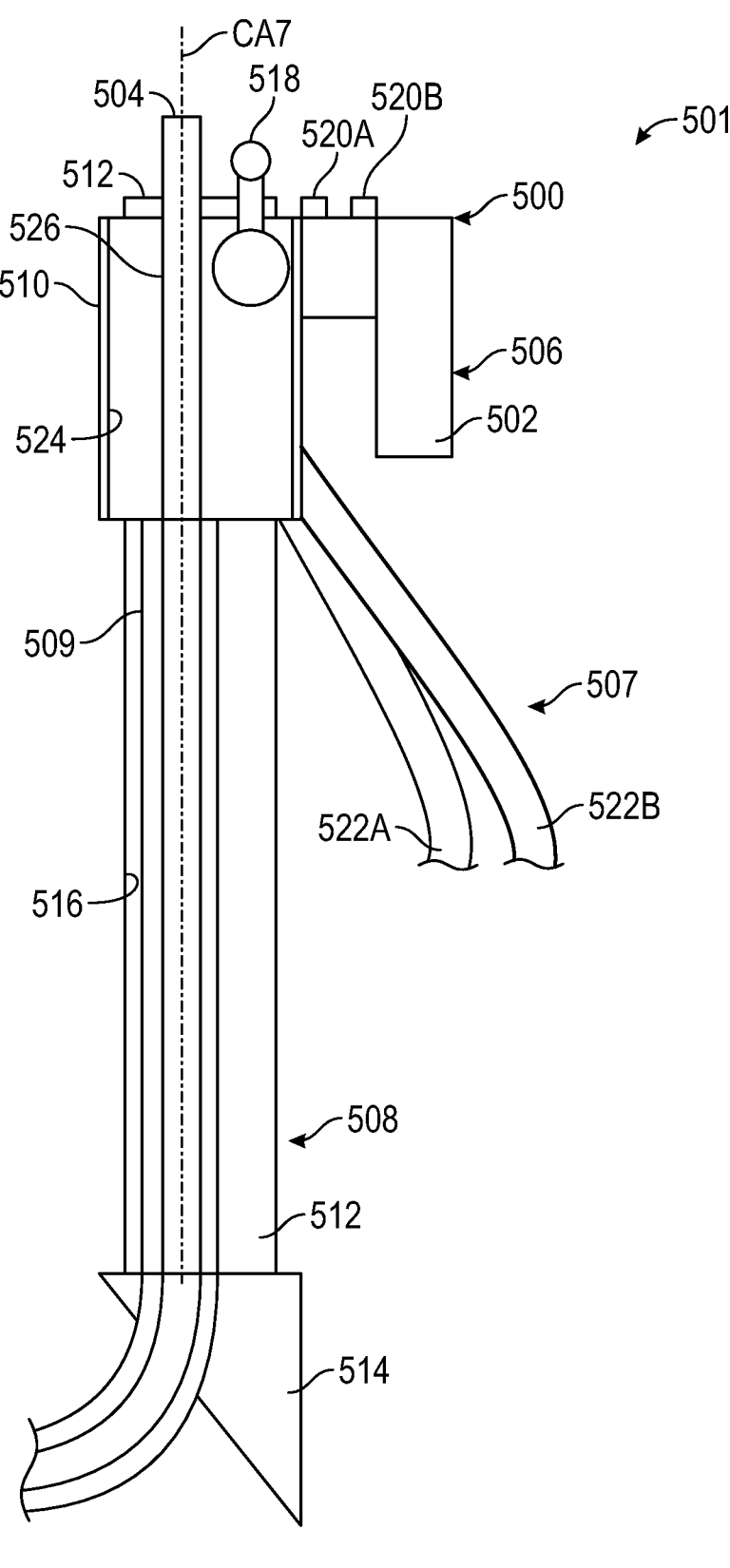
FIG. 14 is a schematic illustration of a controller for an endoscope having a pistol grip and a top-loading therapy device.

FIG. 14 is a schematic illustration of controller 500 for endoscope 501 having pistol grip 502 and top-loading therapy device 504. Controller 500 can comprise handpiece 506, control input 507, attachment piece 508 and shaft 509. Handpiece 506 can comprise slide body 510 from which pistol grip 502 extends. Attachment piece 508 can comprise slide post 512 and coupler 514. Therapy device 504 can be configured similarly as intervention device 305 (FIG. 8A) or instrument 63 (FIG. 3C). In examples, controller 500 can be connected to the proximal end of shaft 202 of FIG. 6 or shaft 252 of FIG. 7.

Attachment piece 508 can be configured similarly as attachment piece 304 of FIGS. 8A-11. Slide post 512 can extend from coupler 514 along central axis CA7. Slide post 512 can comprise an elongate rigid body that can be maintained in a fixed position relative to coupler 514. In examples, slide post 512 can be made of rigid plastic or metal. In additional examples, slide post 512 can be made of a flexible tube, such as a gooseneck tube. Slide post 512 can include internal passage 516 or lumen to allow for passage of components therethrough, such as shaft 509 extending from slide body 510.

Slide body 510 can comprise a platform for mounting other components of controller 500. For example, actuator 518 for operating pull wires within shaft 509 and button 520A and button 520B for operating control input 507. For example, button 520A can be configured to operate fluid tube 522A and button 520B can be configured to operate power cable 522B.

Slide body 510 can comprise a body having internal passage 524 configured to fit around slide post 512. Slide body 510 can also include passage 526 for receiving shaft 509. Shaft 509 can be immobilized relative to slide body 510 to facilitate pushing and pulling and rotation of shaft 509 by slide body 510. Slide body 510 can extend along a handle axis that is coaxial with axis CA7 of slide post 512. Slide body 510 can move relative to slide post 512 and slide post 512 can extend further out of the top or proximal surface of slide body 510 as slide body 510 is advanced further down along slide post 512 toward coupler 514. As with other examples described herein, slide body 510 can be frictionally engaged with slide post 512 and can be locked in place with various locking mechanisms actuatable by an operator.

Shaft 509 can be attached to slide body 510 such that shaft 509 can be pushed further out of slide post 512 and coupler 514 as slide body 510 is advanced further down along slide post 512 toward coupler 514. Furthermore, rotation of slide body 510 about slide post 512 can cause shaft 509 to rotate within slide post 512. Shaft 509 can be anchored or attached to slide body 510 in various manner to facilitate coordinated or commensurate axial and rotational movement with slide body 510.

Pistol grip 502 can be connected to slide body 510 to provide an ergonomic grip for slide body 510. Button 520A and button 520B can be positioned on slide body 510 to be readily accessible by a thumb of a hand grasping pistol grip 502. Likewise, actuator 518 can be positioned on slide body 510 to be readily accessible by a thumb of a hand grasping pistol grip 502.

Figure 15A:
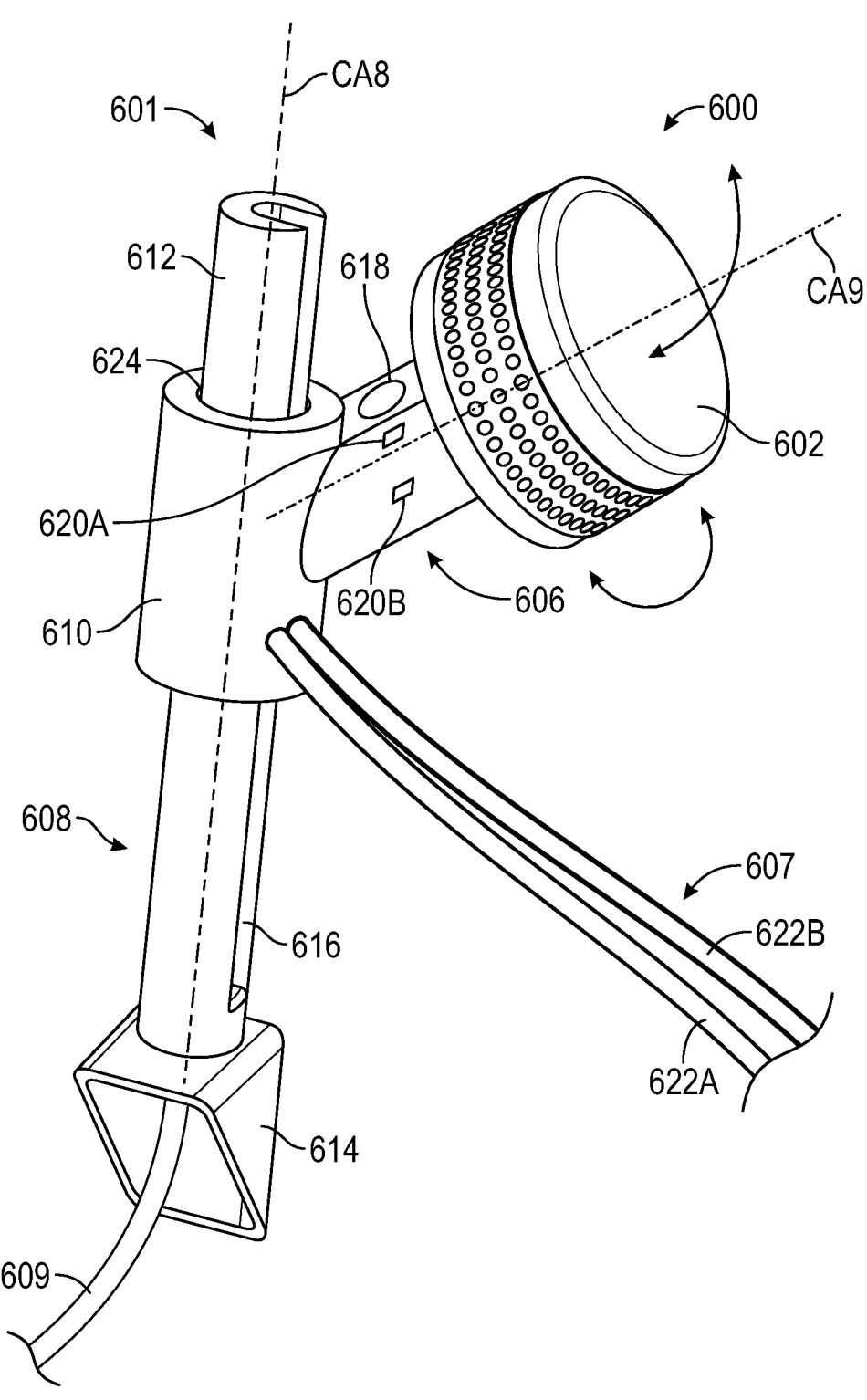
FIG. 15A is a schematic illustration of a controller for an endoscope having a rotatable knob connected to an attachment piece via a pivoting coupler.
Figure 15B:
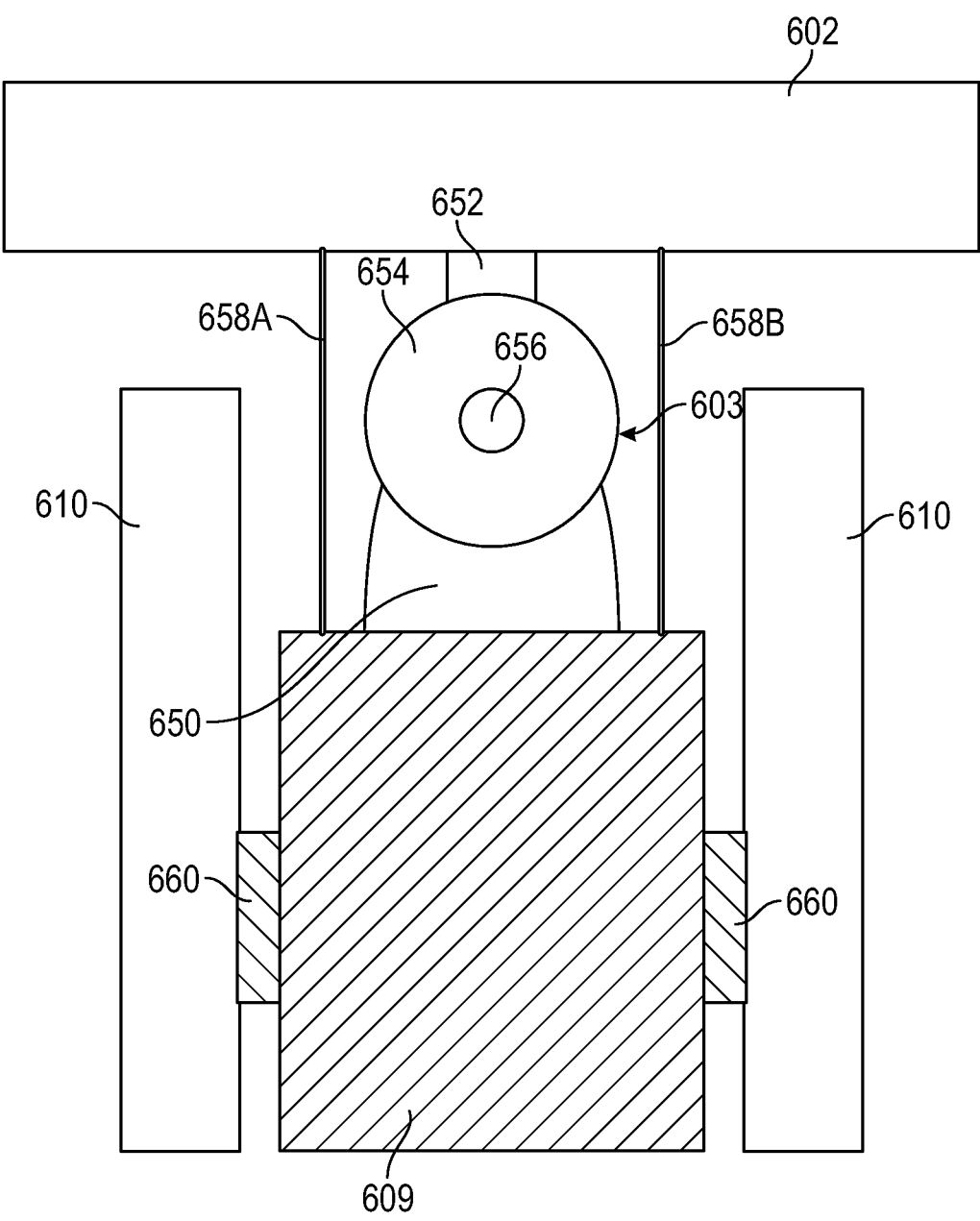
FIG. 15B is a schematic cross-sectional illustration of the pivoting coupler of FIG. 15A.

FIG. 15A is a schematic illustration of controller 600 for endoscope 601 having knob 602 connected to handpiece 606 via pivoting coupler 603 (FIG. 15B). FIG. 15B is a schematic cross-sectional illustration of pivoting coupler 603 of FIG. 15A. FIGS. 15A and 15B are discussed concurrently.

Controller 600 can additionally comprise control input 607, attachment piece 608 and shaft 609. Handpiece 606 can comprise slide body 610 to which knob 602 can be attached. Attachment piece 608 can comprise slide post 612 and coupler 614. In examples, controller 600 can be connected to the proximal end of shaft 202 of FIG. 6 or shaft 252 of FIG. 7.

Attachment piece 608 can be configured similarly as attachment piece 304 of FIGS. 8A-11. Slide post 612 can extend from coupler 614 along central axis CA8. Slide post 612 can comprise an elongate rigid body that can be maintained in a fixed position relative to coupler 614. In examples, slide post 612 can be made of rigid plastic or metal. In additional examples, slide post 612 can be made of a flexible tube, such as a gooseneck tube. Slide post 612 can include internal passage 616 or lumen to allow for passage of components therethrough, such as shaft 609 extending from slide body 610.

Slide body 610 can comprise a platform for mounting other components of controller 600. For example, knob 602 for operating pull wires within shaft 609 and button 620A and button 620B for operating control input 607. For example, button 620A can be configured to operate fluid tube 622A and button 620B can be configured to operate power cable 622B.

Slide body 610 can comprise a body having internal passage 624 configured to fit around slide post 612. Slide body 610 can also include an internal passage for receiving shaft 609. Access opening 618 can be included on slide body 610 to allow a therapy device, such as intervention device 305 (FIG. 8A) or instrument 63 (FIG. 3C), to be inserted into shaft 609. Slide body 610 can extend along a handle axis that is coaxial with axis CA8 of slide post 612. Slide body 610 can move relative to slide post 612 and slide post 612 can extend further out of the top or proximal surface of slide body 610 as slide body 610 is advanced further down along slide post 612 toward coupler 614.

Shaft 609 can be attached to slide body 610 such that shaft 609 can be pushed further out of slide post 612 and coupler 614 as slide body 610 is advanced further down along slide post 612 toward coupler 614. However, rather than rotating slide body 610 about slide post 612 and axis CA8 to induce rotation of shaft 609, knob 602 can be rotated about axis CA9 to rotate shaft 609. As with other examples described herein, slide body 610 can be frictionally engaged with slide post 612 and can be locked in place with various locking mechanisms actuatable by an operator.

As can be seen in FIG. 15B, pivoting coupler 603 can connect knob 602 to shaft 609. Pivoting coupler 603 can function as a joystick to allow for rotation and bending of shaft 609. Pivoting coupler 603 can comprise bracket 650 extending from shaft 609 and post 652 extending from knob 602. Post 652 can include plate 654 that can be attached to bracket 650 by pivot pin 656. Pull wire 658A and pull wire 658B can extend from shaft 609 and be connected to knob 602. Shaft 609 can be supported within slide body 610 via bracket 660. Bracket 660 can be configured to hold shaft 609 in place along axis CA9 such that movement of slide body 610 along axis CA8 will produce movement of shaft 609. However, bracket 660 can be configured to allow shaft 609 to rotate within slide body 610. As such, knob 602 can be configured to induce rotation of shaft 609 along axis CA9. For example, rotation of knob 602 can induce rotation of pivot pin 656 and plate 654, which can induce rotation of bracket 650 and shaft 609. Plate 654 and bracket 650 can comprise flat or planar plates to allow rotation of knob 602 to be transmitted to shaft 609, but that permit relative rotation between plate 654 and bracket 650 on pivot pin 656. However, pivot pin 656 can be configured to allow knob 602 to pivot on pivot pin 656 relative to bracket 650. Pivoting of knob 602 on pivot pin 656 can actuate pull wire 658A and pull wire 658B.

The configuration of FIGS. 15A and 15B can allow an operator to provide rotational input to shaft 609 and bending movement to shaft 609 with a single hand, both using wrist movements. For example, medial and lateral wrist movements can cause rotation of knob 602 and shaft 609 and flexion and extension wrist movements can cause pulling of one of pull wire 658A and pull wire 658B. Button 620A and button 620B can be accessed on slide body 610 by the thumb of the hand placed on knob 602.

Figure 16A:
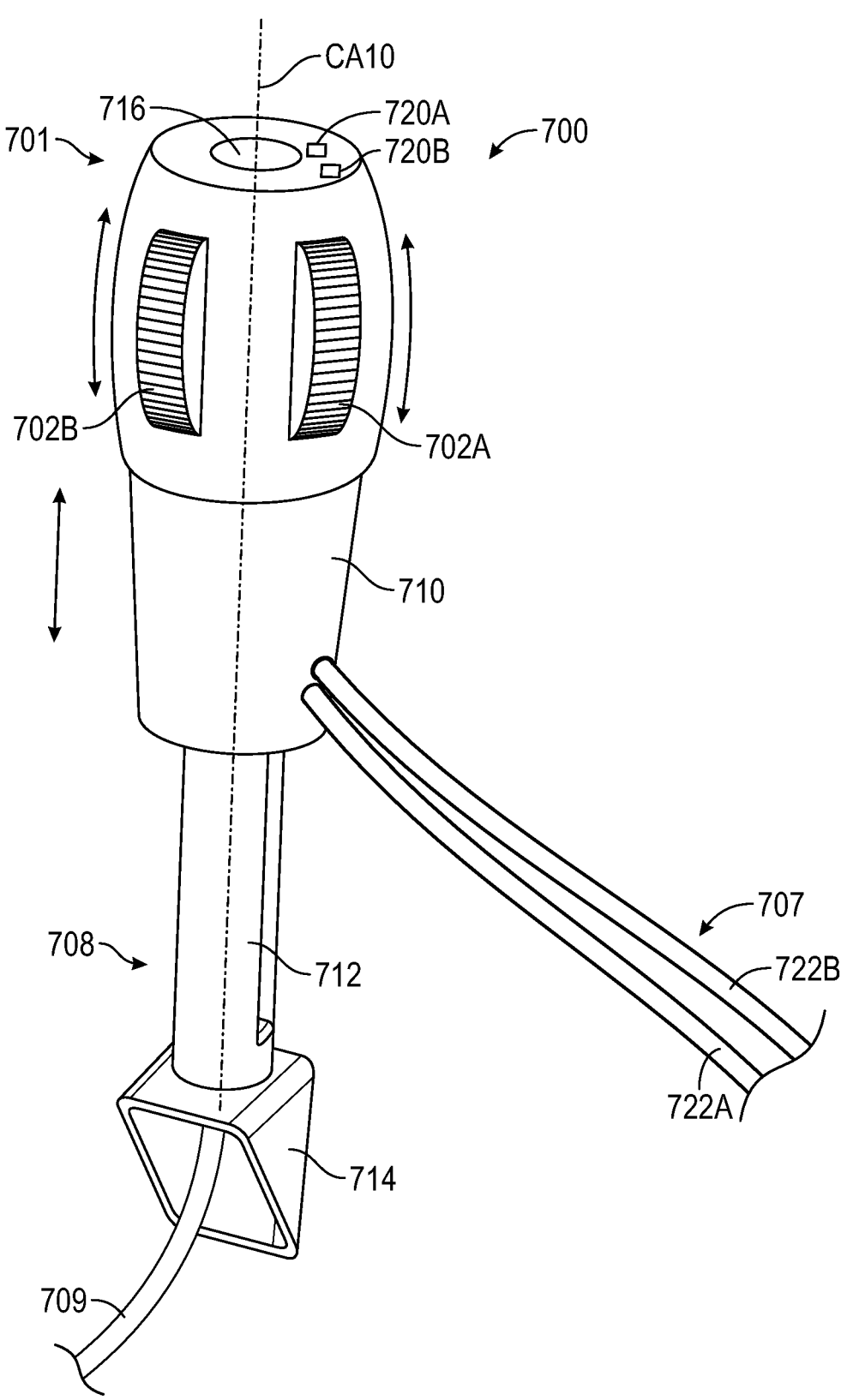
FIG. 16A is a schematic illustration of a controller for an endoscope having a plurality of thumbwheels on a handpiece mounted to an attachment piece.
Figure 16B:
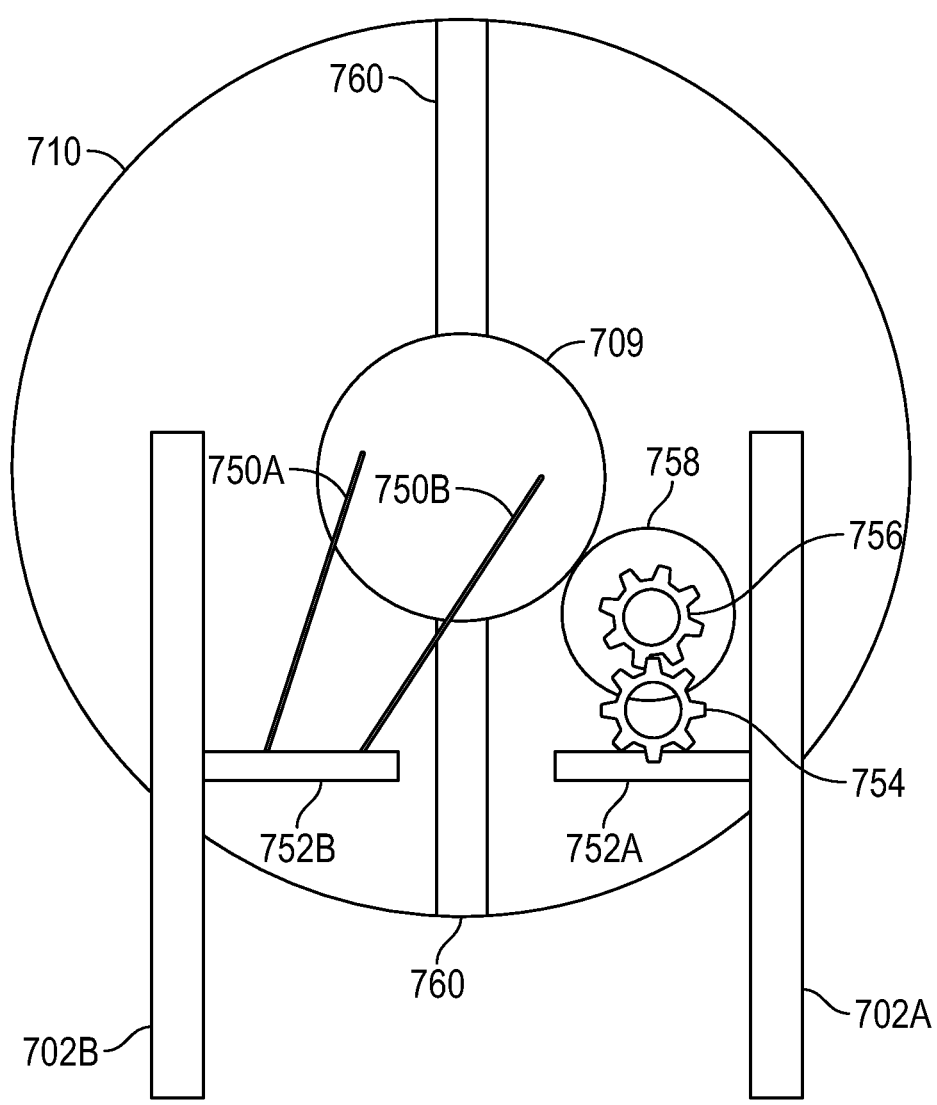
FIG. 16B is a schematic cross-sectional illustration of the thumbwheels of FIG. 16A configured to induce rotation and articulation of a shaft.

FIG. 16A is a schematic illustration of controller 700 for endoscope 701 having thumbwheel 702A and thumbwheel 702B connected to handpiece 704. FIG. 16B is a schematic cross-sectional illustration of thumbwheel 702A and thumb-wheel 702B of FIG. 16A configured to induce rotation and articulation of shaft 709. FIGS. 16A and 16B are discussed concurrently.

Controller 700 can additionally comprise control input 707, attachment piece 708 and shaft 709. Handpiece 706 can comprise slide body 710 to which thumbwheels 702A and 702B can be attached. Attachment piece 708 can comprise slide post 712 and coupler 714. In examples, controller 700 can be connected to the proximal end of shaft 202 of FIG. 6 or shaft 252 of FIG. 7.

Attachment piece 708 can be configured similarly as attachment piece 304 of FIGS. 8A-11. Slide post 712 can extend from coupler 714 along central axis CA10. Slide post 712 can comprise an elongate rigid body that can be maintained in a fixed position relative to coupler 714. In examples, slide post 712 can be made of rigid plastic or metal. In additional examples, slide post 712 can be made of a flexible tube, such as a gooseneck tube. Slide post 712 can include internal passage 716 or lumen to allow for passage of components therethrough, such as shaft 709 extending from slide body 710. Internal passage 716 can also include an access opening on the exterior of slide body 710 to allow for the insertion of a therapy device, such as intervention device 305 (FIG. 8A) or instrument 63 (FIG. 3C), into shaft 709.

Slide body 710 can comprise a platform for mounting other components of controller 700. For example, thumb-wheel 702A for rotating shaft 709 and thumbwheel 702B for operating pull wire 750A and pull wire 750B within shaft 709 can be mounted to slide body 710. Also, button 720A can be configured to operate fluid tube 722A and button 720B can be configured to operate power cable 722B.

Slide body 710 can comprise a body having internal passage 624 configured to fit around slide post 712. Slide body 710 can extend along a handle axis that is coaxial with axis CA10 of slide post 712. Slide body 710 can move relative to slide post 712 and slide post 712 can extend further out of the top or proximal surface of slide body 710 as slide body 710 is advanced further down along slide post 712 toward coupler 714. As with other examples described herein, slide body 710 can be frictionally engaged with slide post 712 and can be locked in place with various locking mechanisms actuatable by an operator.

Shaft 709 can be attached to slide body 710 such that shaft 709 can be pushed further out of slide post 712 and coupler 714 as slide body 710 is advanced further down along slide post 712 toward coupler 714. However, rather than rotating slide body 710 about slide post 712 and axis CA10 to induce rotation of shaft 709, thumbwheel 702A can be rotated to rotate shaft 709.

As can be seen in FIG. 16B, thumbwheel 702A can be mounted within slide body 710 on axle 752A and thumb-wheel 702B can be mounted within slide body 710 on axle 752B. FIG. 16B can comprise a cross-section through slide body 710 looking down toward slide post 712. In examples, axle 752A can comprise a worm gear engaged with drive gear 754. Drive gear 754 can be engaged with output gear 756, which can be coupled to drive wheel 758.

Shaft 709 can be supported within slide body 710 via bracket 760. Bracket 760 can be configured to hold shaft 709 in place along axis CA10 such that movement of slide body 710 along axis CA10 will produce movement of shaft 709. However, bracket 760 can be configured to allow shaft 709 to rotate within slide body 710. As such, thumbwheel 702A can be configured to induce rotation of shaft 709 along axis CA10. For example, rotation of thumbwheel 702A can induce rotation of drive gear 754, which can induce rotation of output gear 756. Output gear 756 can rotate drive wheel 758 which can be frictionally engaged with shaft 709. Drive wheel 758 can comprise a rubber disk that can push shaft 709 when thumbwheel 702A is pushed. Other rotatable rubber discs can be included within slide body 710 to hold shaft 709 in an axial position, but allow for rotation of shaft 709. In examples, the rubber disks can be configured to ride within a groove in shaft 709 to provide axial immobilization while still allowing for rotation. Thumbwheel 702B can be rotated on axle 752B to actuate pull wire 750A and pull wire 750B. A drum or barrel can be mounted on axle 752B to provide pulling capabilities (e.g., increased leverage) of thumbwheel 702B.

The configuration of FIGS. 16A and 16B can allow an operator to provide rotational input to shaft 709 and bending movement to shaft 709 with a single hand using thumb movements. For example, upward movement of thumbwheel 702B can induce bending of shaft 709 in a first direction and downward movement of thumbwheel 702B can induce bending of shaft 709 is a second direction opposite the first direction. For example, upward movement of thumbwheel 702A can induce rotation of shaft 709 about axis CA10 in a first direction and downward movement of thumbwheel 702A can induce rotation of shaft 709 is a second direction opposite the first direction. Button 720A and button 720B can be accessed on slide body 710 by the thumb of the hand placed on slide body 710.

Figure 17:
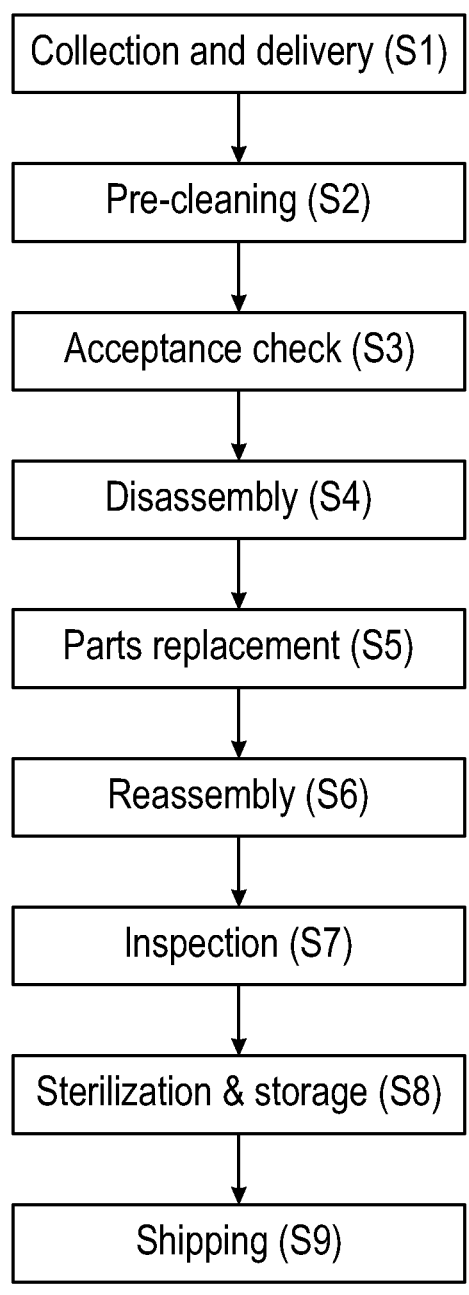
FIG. 17 is a flowchart indicating a reprocessing method for systems, treatment instruments and components disclosed in the present application.

FIG. 17 is a flowchart indicating reprocessing method 800 for treatment instruments disclosed in the present application. The treatment instruments described above, such as controller 300 of FIG. 8A, controller 400 of FIG. 13, controller 500 of FIG. 14, controller 600 of FIG. 15A and controller 700 of FIG. 16A, as well as the insertion sections and working shafts that can be attached thereto, may be disposed of after one use, or may be repeatedly used a plurality of times. In the case of a configuration that is repeatedly used a plurality of times, for example, the reprocessing method shown in FIG. 17 is required or can be used. An operator collects the used treatment instrument after the treatment instrument has been used for treatment and transports the treatment instrument to a factory or the like (Step S1). Then, the operator cleans and sterilizes the collected and transported used treatment instrument (Step S2). Next, the operator performs an acceptance check of the used treatment instrument (Step S3). Subsequently, the operator disassembles the used treatment instrument (Step S4) and replaces some parts of the used treatment instrument with new parts (Step S5). After step S5, the operator assembles a new or reprocessed treatment instrument (Step S6). In some examples, Step S6 can include adding an identifier to indicate the device has been modified from its original condition, such as a adding a label or other marking to designate the device as reprocessed, refurbished or remanufactured. After Step S6, the operator sequentially performs an inspection (Step S7), sterilization and storage (Step S8), and shipping (Step S9) of the new treatment instrument. The treatment instruments according to the present embodiments have ergonomic controllers that can be reprocessed for multiple uses. Therefore, there is advantage that the ergonomic controllers of the present disclosure can reduce the cost of medical procedures.

EXAMPLES

Example 1 is a controller for an auxiliary endoscope, the controller comprising: a coupling piece for attaching to a main endoscope; a handpiece connected to the coupling piece; a working shaft extending from the handpiece and extending into the coupling piece; and a first control feature located on the handpiece for operating a pull wire extending through the working shaft, the pull wire configured to steer the auxiliary endoscope; wherein the handpiece can be moved relative to the coupling piece to adjust a position of the auxiliary endoscope relative to the main endoscope.

In Example 2, the subject matter of Example 1 optionally includes wherein the handpiece can be moved to adjust an amount of the working shaft extending through the coupling piece.

In Example 3, the subject matter of Example 2 optionally includes wherein the handpiece is axially translatable relative to the coupling piece along a slide axis.

In Example 4, the subject matter of Example 3 optionally includes wherein the coupling piece comprises a slide post extending along the slide axis and that is configured to be coupled to the main endoscope, wherein the handpiece is configured to slide along the slide post.

In Example 5, the subject matter of Example 4 optionally includes wherein the handpiece is connected to the slide post via a receiver that facilitates rotation of the handpiece relative to the coupling piece.

In Example 6, the subject matter of Example 5 optionally includes wherein the handpiece extends along a handpiece axis that is oblique relative to an axis of the receiver.

In Example 7, the subject matter of any one or more of Examples 5-6 optionally include wherein the handpiece extends along a handpiece axis that is aligned with an axis of the receiver.

In Example 8, the subject matter of any one or more of Examples 4-7 optionally include wherein the handpiece extends along a handpiece axis that is coaxial with the slide post.

In Example 9, the subject matter of any one or more of Examples 4-8 optionally include wherein rotation of the handpiece produces rotation of the working shaft.

In Example 10, the subject matter of Example 9 optionally includes wherein the first control feature comprises a joystick that can be pivoted to actuate the pull wire and rotated to rotate the working shaft.

In Example 11, the subject matter of any one or more of Examples 9-10 optionally include wherein the handpiece can be directly rotated about the slide post to rotate the working shaft.

In Example 12, the subject matter of Example 11 optionally includes wherein the first control feature comprises a first thumbwheel attached to the handpiece.

In Example 13, the subject matter of Example 12 optionally includes wherein the handpiece comprises a second control feature configured to provide rotation of the working shaft relative to the handpiece.

In Example 14, the subject matter of Example 13 optionally includes wherein the second control feature comprises a second thumbwheel connected to a drive wheel by a gear system, the drive wheel configured to rotate the working shaft.

In Example 15, the subject matter of any one or more of Examples 11-14 optionally include wherein the handpiece comprises: a main body configured to slide along the slide post; and a pistol grip extending from the main body.

In Example 16, the subject matter of any one or more of Examples 1-15 optionally include wherein the first control feature comprises a lever attached to the handpiece.

In Example 17, the subject matter of any one or more of Examples 1-16 optionally include an aperture located in the handpiece in communication with an opening in the working shaft connecting to a working channel of the working shaft.

In Example 18, the subject matter of any one or more of Examples 1-17 optionally include control inputs connected to the working shaft for providing interventional functionality to a distal tip of the working shaft; and buttons positioned on the handpiece to operate the control inputs.

In Example 19, the subject matter of any one or more of Examples 1-18 optionally include a locking mechanism to prevent movement of the handpiece relative to the coupling piece.

In Example 20, the subject matter of any one or more of Examples 1-19 optionally include wherein the coupling piece comprises a coupler housing configured to attach to the main endoscope over a port for receiving the auxiliary endoscope.

Example 21 is an endoscopy system comprising: a main scope comprising: a main controller; an elongate shaft extending from the main controller, the elongate shaft having a working channel extending therethough; and an access port located on the main controller to access the working channel; and an auxiliary scope comprising: a slide post configured to be coupled to the access port; an auxiliary controller slidably attached to the slide post; an auxiliary shaft configured to extend from the auxiliary controller through the slide post and into the working channel of the main scope; and a control input extending into the auxiliary controller to connect to the auxiliary shaft.

In Example 22, the subject matter of Example 21 optionally includes wherein the auxiliary controller comprises: a handpiece including a first control feature for operating pull wires within the auxiliary shaft; a swivel body extending from the handpiece; a receiver slidably attached to the slide post to receive the swivel body, wherein the handpiece can be rotated at the swivel body to rotate the auxiliary shaft within the slide post; and an access opening in the swivel body to receive an intervention device into the auxiliary shaft.

In Example 23, the subject matter of Example 22 optionally includes wherein the handpiece is positioned by the swivel body and the receiver to be approximately parallel to the main controller.

In Example 24, the subject matter of any one or more of Examples 21-23 optionally include wherein the auxiliary controller comprises: a handpiece including a first control feature for operating pull wires within the auxiliary shaft; a receiver slidably attached to the slide post to receive the handpiece, wherein the handpiece can be rotated in the receiver to rotate the auxiliary shaft within the slide post; and an access opening in the handpiece to receive an intervention device into the auxiliary shaft.

In Example 25, the subject matter of Example 24 optionally includes a swivel ring connecting the control input to the handpiece to allow the control input to rotate relative to the handpiece.

In Example 26, the subject matter of any one or more of Examples 21-25 optionally include wherein the auxiliary controller comprises: a slide body including a first control feature for operating pull wires within the auxiliary shaft, wherein the slide body is configured to slide over the slide post and rotate about the slide post; and a pistol grip extending from the slide body.

In Example 27, the subject matter of Example 26 optionally includes wherein the slide body includes one or more buttons for operating the control input.

In Example 28, the subject matter of any one or more of Examples 21-27 optionally include wherein the auxiliary controller comprises: a slide body configured to slide over the slide post; a knob connected to the slide body, wherein the knob is configured to operate pull wires within the auxiliary shaft and rotate the auxiliary shaft relative to the slide post; and an access opening in the slide body to receive an intervention device into the auxiliary shaft.

In Example 29, the subject matter of Example 28 optionally includes wherein the knob is connected to the auxiliary shaft via a pivoting coupler configured to provide side-to-side movement of the knob relative to the auxiliary shaft and to drive rotation of the auxiliary shaft via a pinned connection between flat plates.

In Example 30, the subject matter of any one or more of Examples 21-29 optionally include wherein the auxiliary controller comprises: a slide body configured to slide over the slide post; a first thumbwheel for operating pull wires within the auxiliary shaft; and a second thumbwheel for rotating the auxiliary shaft within the slide post.

In Example 31, the subject matter of Example 30 optionally includes wherein the second thumbwheel is connected to the auxiliary shaft via a worm gear system configured to rotate a drive wheel.

Each of these non-limiting examples can stand on its own, or can be combined in various permutations or combinations with one or more of the other examples.

Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A controller for an auxiliary endoscope, the controller comprising:
a coupling piece for attaching to a main endoscope;
a slide post extending from the coupling piece along a slide axis;
a receiver connected to the slide post, the receiver extending along a receiver axis;
a handpiece connected to the receiver;
a working shaft extending from the handpiece and extending into the receiver, the slide post and the coupling piece; and
a first control feature located on the handpiece for operating a pull wire extending through the working shaft, the pull wire configured to steer the auxiliary endoscope;
wherein the handpiece can be moved relative to the coupling piece to adjust a position of the auxiliary endoscope relative to the main endoscope;
wherein the slide axis and the receiver axis are oblique; and
wherein the slide post includes a slot to allow the working shaft to extend from the handpiece into the slide post to enter the coupling piece.

2. The controller of claim 1, wherein the slide post is straight along a length from a first end to a second end and the handpiece can be moved along the length of the slide post to adjust an amount of the working shaft extending through the coupling piece.

3. The controller of claim 2, wherein the slot extends along the length of the slide post so that the handpiece is axially translatable relative to the coupling piece along the slide axis with the working shaft extending through the slot.

4. The controller of claim 1, wherein the slide post is configured to be coupled to the main endoscope via the coupling piece, wherein the handpiece is configured to slide along the slide post via the receiver.

5. The controller of claim 1, wherein the receiver comprises a socket and the handpiece comprises a swivel body rotatably coupled with the socket to facilitate rotation of the handpiece relative to the coupling piece.

6. The controller of claim 5, wherein the handpiece extends along a handpiece axis that is oblique relative to the receiver axis of the receiver.

7. The controller of claim 6, wherein:
the slide axis, the receiver axis and the handpiece axis are different from each other.

8. The controller of claim 5, wherein:
the receiver is connected to the slide post via a slide body configured to slide along the slide post; and
the slide post is configured to extend through the slide body.

9. The controller of claim 4, wherein rotation of the handpiece produces rotation of the working shaft.

10. The controller of claim 7, wherein the handpiece is arranged to be offset from the slide post so that the handpiece does not intersect with the slide post.

11. The controller of claim 1, wherein the first control feature comprises a lever attached to the handpiece.

12. The controller of claim 1, further comprising an aperture located in the handpiece in communication with an opening in the working shaft connecting to a working channel of the working shaft.

13. The controller of claim 1, further comprising:
control inputs connected to the working shaft for providing interventional functionality to a distal tip of the working shaft; and
buttons positioned on the handpiece to operate the control inputs.

14. The controller of claim 1, further comprising a locking mechanism to prevent movement of the handpiece relative to the coupling piece.

15. The controller of claim 1, wherein the coupling piece comprises a coupler housing configured to attach to the main endoscope over a port for receiving the auxiliary endoscope.

16. An endoscopy system comprising:
a main scope comprising:
a main controller;
an elongate shaft extending from the main controller, the elongate shaft having a working channel extending therethough; and
an access port located on the main controller to access the working channel; and
an auxiliary scope comprising:
a coupling piece for attaching to the access port of the main scope;
a slide post configured to be coupled to the access port via the coupling piece, the slide post extending along a slide axis;
a receiver connected to the slide post, the receiver extending along a receiver axis;
an auxiliary controller slidably attached to the slide post via the receiver;
an auxiliary shaft configured to extend from the auxiliary controller through the receiver, the slide post and the coupling piece and into the working channel of the main scope; and
a control input extending into the auxiliary controller to connect to the auxiliary shaft;
wherein the slide axis and the receiver axis are oblique; and
wherein the slide post includes a slot to allow the auxiliary shaft to extend from the auxiliary controller into the slide post to enter the coupling piece.

17. The endoscopy system of claim 16, wherein the auxiliary controller comprises:
a handpiece including a first control feature for operating pull wires within the auxiliary shaft;
a swivel body extending from the handpiece to seat within the receiver,
wherein the handpiece can be rotated at the swivel body to rotate the auxiliary shaft within the slide post; and
an access opening in the swivel body to receive an intervention device into the auxiliary shaft.

18. The endoscopy system of claim 17, wherein the handpiece is positioned by the swivel body and the receiver to be approximately parallel to the main controller.

*   *   *   *   *